US008377110B2

(12) United States Patent
Douglas et al.

(10) Patent No.: US 8,377,110 B2
(45) Date of Patent: Feb. 19, 2013

(54) ENDOLUMENAL VASCULAR PROSTHESIS WITH NEOINTIMA INHIBITING POLYMERIC SLEEVE

(75) Inventors: Myles S. Douglas, Gardnerville, NV (US); Frank M. Zeng, Irvine, CA (US); Brian C. Gray, Orange, CA (US)

(73) Assignee: Endologix, Inc., Irvine, CA (US)

( * ) Notice: Subject to any disclaimer, the term of this patent is extended or adjusted under 35 U.S.C. 154(b) by 200 days.

(21) Appl. No.: 10/820,455

(22) Filed: Apr. 8, 2004

(65) Prior Publication Data

US 2005/0228480 A1    Oct. 13, 2005

(51) Int. Cl.
*A61F 2/06* (2006.01)
(52) U.S. Cl. ........................................ 623/1.13
(58) Field of Classification Search .......... 623/1.13, 623/1.14, 1.23, 1.39, 1.4
See application file for complete search history.

(56) References Cited

U.S. PATENT DOCUMENTS

| | | | |
|---|---|---|---|
| 3,953,566 A | 4/1976 | Gore | |
| 4,187,390 A | 2/1980 | Gore | |
| 4,478,665 A | 10/1984 | Hubis | |
| 4,482,516 A | 11/1984 | Bowman | |
| 4,816,339 A | 3/1989 | Tu | |
| 5,071,609 A | 12/1991 | Tu | |
| 5,175,052 A * | 12/1992 | Tokuda et al. | 428/355 AC |
| 5,197,976 A | 3/1993 | Herweck | |
| 5,370,681 A | 12/1994 | Herweck | |
| 5,411,550 A | 5/1995 | Herweck | |
| 5,474,824 A | 12/1995 | Martakos | |
| 5,769,884 A * | 6/1998 | Solovay | 623/1.13 |
| 5,824,046 A * | 10/1998 | Smith et al. | 623/1.13 |
| 5,843,161 A * | 12/1998 | Solovay | 623/1.13 |
| 5,858,505 A | 1/1999 | Moen | |
| 5,861,033 A | 1/1999 | Martakos | |
| 5,955,016 A | 9/1999 | Goldfarb | |
| 5,980,799 A | 11/1999 | Martakos | |
| 6,039,755 A | 3/2000 | Edwin et al. | |
| 6,077,296 A | 6/2000 | Shokoohi et al. | |
| 6,090,128 A | 7/2000 | Douglas | |
| 6,156,063 A | 12/2000 | Douglas | |
| 6,187,036 B1 | 2/2001 | Shaolian et al. | |
| 6,197,049 B1 * | 3/2001 | Shaolian et al. | 623/1.35 |
| 6,203,735 B1 | 3/2001 | Edwin | |
| 6,210,422 B1 | 4/2001 | Douglas | |

(Continued)

FOREIGN PATENT DOCUMENTS

JP    51-48597    6/1993
JP    07-024072    1/1995

(Continued)

OTHER PUBLICATIONS

Co-pending U.S. Appl. No. 10/755,703, filed Jan. 12, 2004, titled Endoluminal Vascular Prosthesis.

(Continued)

*Primary Examiner* — Melanie Tyson
(74) *Attorney, Agent, or Firm* — Knobbe, Martens, Olson & Bear, LLP

(57) ABSTRACT

The present invention is related to a low profile endolumenal prosthesis. The prosthesis comprises a radially expandable tubular wire support and an expanded PTFE membrane. The density, wall thickness and intranodal distance of the ePTFE are selected to inhibit the formation and nourishment of a viable neointima on the inner surface of the prosthesis, through the ePTFE membrane.

32 Claims, 26 Drawing Sheets

U.S. PATENT DOCUMENTS

| | | | |
|---|---|---|---|
| 6,261,316 B1 | 7/2001 | Shaolian et al. | |
| 6,331,190 B1 | 12/2001 | Shokoohi et al. | |
| 6,364,903 B2 | 4/2002 | Tseng | |
| 6,379,382 B1 * | 4/2002 | Yang | 623/1.42 |
| 6,436,135 B1 | 8/2002 | Goldfarb | |
| 6,440,161 B1 | 8/2002 | Madrid et al. | |
| 6,451,047 B2 * | 9/2002 | McCrea et al. | 623/1.13 |
| 6,471,687 B2 | 10/2002 | Butler | |
| 6,500,202 B1 | 12/2002 | Shaolian et al. | |
| 6,508,835 B1 | 1/2003 | Shaolian et al. | |
| 6,517,571 B1 | 2/2003 | Brauker | |
| 6,540,773 B2 | 4/2003 | Dong | |
| 6,554,855 B1 | 4/2003 | Dong | |
| 6,660,030 B2 | 12/2003 | Shaolian et al. | |
| 6,663,665 B2 | 12/2003 | Shaolian et al. | |
| 6,689,157 B2 | 2/2004 | Madrid et al. | |
| 6,719,783 B2 | 4/2004 | Lentz | |
| 6,733,523 B2 | 5/2004 | Shaolian et al. | |
| 6,752,826 B2 * | 6/2004 | Holloway et al. | 623/1.13 |
| 6,755,856 B2 | 6/2004 | Firens et al. | |
| 6,890,463 B2 | 5/2005 | Martakos | |
| 6,926,735 B2 | 8/2005 | Henderson | |
| 6,939,372 B2 | 9/2005 | Dong | |
| 6,951,572 B1 | 10/2005 | Douglas | |
| 6,953,475 B2 | 10/2005 | Shaolian et al. | |
| 7,041,127 B2 | 5/2006 | Ledergerber | |
| 7,186,263 B2 | 3/2007 | Golds | |
| 7,306,756 B2 | 12/2007 | Edwin | |
| 7,465,483 B2 | 12/2008 | Colone | |
| 7,510,571 B2 | 3/2009 | Spiridigliozzi | |
| 2001/0025131 A1 | 9/2001 | Edwin | |
| 2002/0042645 A1 | 4/2002 | Shannon | |
| 2003/0017775 A1 | 1/2003 | Sowinski | |
| 2003/0028240 A1 | 2/2003 | Nolting | |
| 2003/0074049 A1 * | 4/2003 | Hoganson et al. | 623/1.13 |
| 2003/0139806 A1 | 7/2003 | Haverkost | |
| 2004/0049264 A1 | 3/2004 | Sowinski | |
| 2004/0054397 A1 | 3/2004 | Smith | |
| 2004/0098087 A1 | 5/2004 | Madrid et al. | |
| 2004/0122509 A1 | 6/2004 | Brodeur | |
| 2004/0167618 A1 | 8/2004 | Shaolian et al. | |
| 2005/0228480 A1 | 10/2005 | Douglas et al. | |
| 2005/0245891 A1 | 11/2005 | McCormick et al. | |
| 2005/0246012 A1 | 11/2005 | Henderson | |
| 2005/0288772 A1 | 12/2005 | Douglas | |
| 2006/0020320 A1 | 1/2006 | Shaolian et al. | |
| 2006/0264138 A1 | 11/2006 | Sowinski | |
| 2006/0271163 A1 | 11/2006 | Shokoohi et al. | |
| 2006/0271164 A1 | 11/2006 | Shaolian et al. | |
| 2006/0287713 A1 | 12/2006 | Douglas et al. | |
| 2008/0143011 A1 | 6/2008 | Colone | |
| 2009/0125092 A1 | 5/2009 | McCrea | |

FOREIGN PATENT DOCUMENTS

| | | |
|---|---|---|
| WO | WO 90/14054 | 11/1990 |
| WO | WO 98/00090 | 1/1998 |
| WO | WO 00/33769 | 6/2000 |
| WO | WO 01/39696 A | 6/2001 |
| WO | WO 02/39888 A | 5/2002 |
| WO | WO 03/037396 | 5/2003 |
| WO | WO 03/053495 | 7/2003 |

OTHER PUBLICATIONS

Co-pending U.S. Appl. No. 11/623,679, filed Jan. 26, 2007, titled Endoluminal Vascular Prosthesis.
Co-pending U.S. Appl. No. 10/119,525, filed Apr. 8, 2002, titled Self Expanding Bifurcated Endovascular Prosthesis.
Co-pending U.S. Appl. No. 11/580,201, filed Oct. 12, 2006, titled Method and Apparatus for Decompressing Aneurysms.
Co-pending U.S. Appl. No. 11/522,292, filed Sep. 15, 2006, titled Multi-Segmented Graft Deployment System.
Co-pending U.S. Appl. No. 11/623,022, filed Jan. 12, 2007, titled Dual Concentric Guidewire and Methods of Bifurcated Graft Deployment.
Co-pending U.S. Appl. No. 10/764,991, filed Jan. 26, 2004, titled Implantable Vascular Graft.
Co-pending U.S. Appl. No. 10/690,227, filed Oct. 21, 2003, titled Single Puncture Bifurcation Graft Deployment System.
Matsumoto, et al., Application of Porous PolyTetrafluoroethylene to Artificial Blood Vessel, First Report: Application to the Peripheral Artery, Artificial Organs, vol. 1, No. 1, pp. 44-47 (1972).
Matsumoto, et al., Experimental Studies on Expanded Polytetraflouroethylene as Vascular Prosthesis—The Second Report: Its Applicability to Veins, Artificial Organs, vol. 2, No. 5, pp. 1-33, (1973); Japanese with English translation.
Matsumoto, et al., A New Vascular Prosthesis for a Small Caliber Artery, Surgery, vol. 74, No. 4, pp. 519-523 (Oct. 1973).
Volder, J.G.R., et al., A-V Shunts Created in New Ways, Transactions American Society for Artificial Internal Organs, vol. XIX, pp. 38-42 (1973).
Soyer, et al., A New Venous Prosthesis, Surgery, vol. 72, No. 6, pp. 864-872 (Dec. 1972).
Campbell, et al., Expanded Polytetrafluoro-Ethylene as a Small Artery Substitute, Transactions American Society for Artificial Organs, vol. XX-A, pp. 86-90 (1974).
Goldfarb, et al., Expanded Polytetrafluoroethylene (PTFE): A Superior Biocompatible Material for Vascular Prosthesis, Proceedings of the San Diego Biomedical Symposium, vol. 14, pp. 451-456 (1975).
Wesolowski, Artificial Arteries, AORN Journal, pp. 35-50 (Jan. 1968).
Campbell, et al., A Small Arterial Substitute: Expanded Microporous Polytetrafluoroethylene: Patency Versus Porosity, Annals of Surgery, vol. 182, No. 2, (Aug. 1975).
Florian, et al., Small Vessel Replacement with Gore-tex (Expanded Polytetrafluoroethylene), Archives of Surgery, vol. III, pp. 267-270 (Mar. 1976).
Decision on Motions, *Cooper v. Goldfarb* Interference, Dec. 18, 1985.
Remand to Examiner, *Cooper v. Goldfarb* Interference, May 29, 1986.
Final Decision, *Cooper v Goldfarb* Interference, Oct. 18, 1995.
Special Master's Report and Recommendations on Claim Construction of Goldfarb Claims, *Bard v. Gore* case, Oct. 24, 2005.
Order Adopting Special Master's report, *Bard v. Gore*, Sep. 28, 2006.
Order denying Summary Judgment re Invalidity, *Bard v. Gore*, Sep. 30, 2004.
Order denying JMOL regarding Anticipation by Matsumoto, *Bard v Gore*, Jul. 29, 2008.
Order denying JMOL re Obviousness, *Bard v. Gore* case, Jul. 29, 2008.
Order denying Gore Motions re Obviousness, *Bard v. Gore* case, Mar. 31, 2009.
Docket from *Goldfarb v. Cooper* Interference, No. 101,100, Apr. 4, 2001.
Docket from the *Bard v. Gore* case, No. CV-03-0597-PHX-MHM, Mar. 28, 2003.
Brief, Motion of Junior Party Goldfarb to Dissolve Count 1, from *Goldfarb v. Cooper* Interference, May 4, 1984.
Brief, Senior Party Cooper's Opposition to the Motion of Junior Party Goldfarb to Dissolve Count 1, Interference, Nov. 5, 1984.
Federal Circuit Decision, *Cooper v. Goldfarb*, 154 F.3d 1321 (Fed. Cir. 1998)—Sep. 1, 1998.
Federal Circuit Decision #2, *Cooper v. Goldfarb*, 240 F.3d 1378 (Fed. Cir. 2001)—Mar. 2, 2001.
Gore's Brief Concerning Construction of the Claims—Jan. 14, 2005.
Gore's Response to Plaintiffs' Brief Concerning Construction of the Claims—Feb. 4, 2005.
Gore's Objections to Selected Portions of the Special Master's Report—Nov. 7, 2005.
Plaintiff's Comments and Objections to the Special Master's Report—Nov. 7, 2005.
Digel, W.A. (ed.), *Expanded "Teflon" TFE Opens New Range of Applications*, The Journal of Teflon, vol. 12, No. 3, pp. 3-4, Sep.-Nov. 1971.
*W.L. Gore & Associates, Inc.* and *Gore Enterprise Holdings, Inc.* (Plaintiff) vs. *Medtronic, Inc., Medtronic USA, Inc., and Medtronic Cardiovascular, Inc.* (Defendant) in the United States District Court for the Easter District of Virginia; Case No. 2:10CV441; Defendant's Answer and Counterclaims.

* cited by examiner

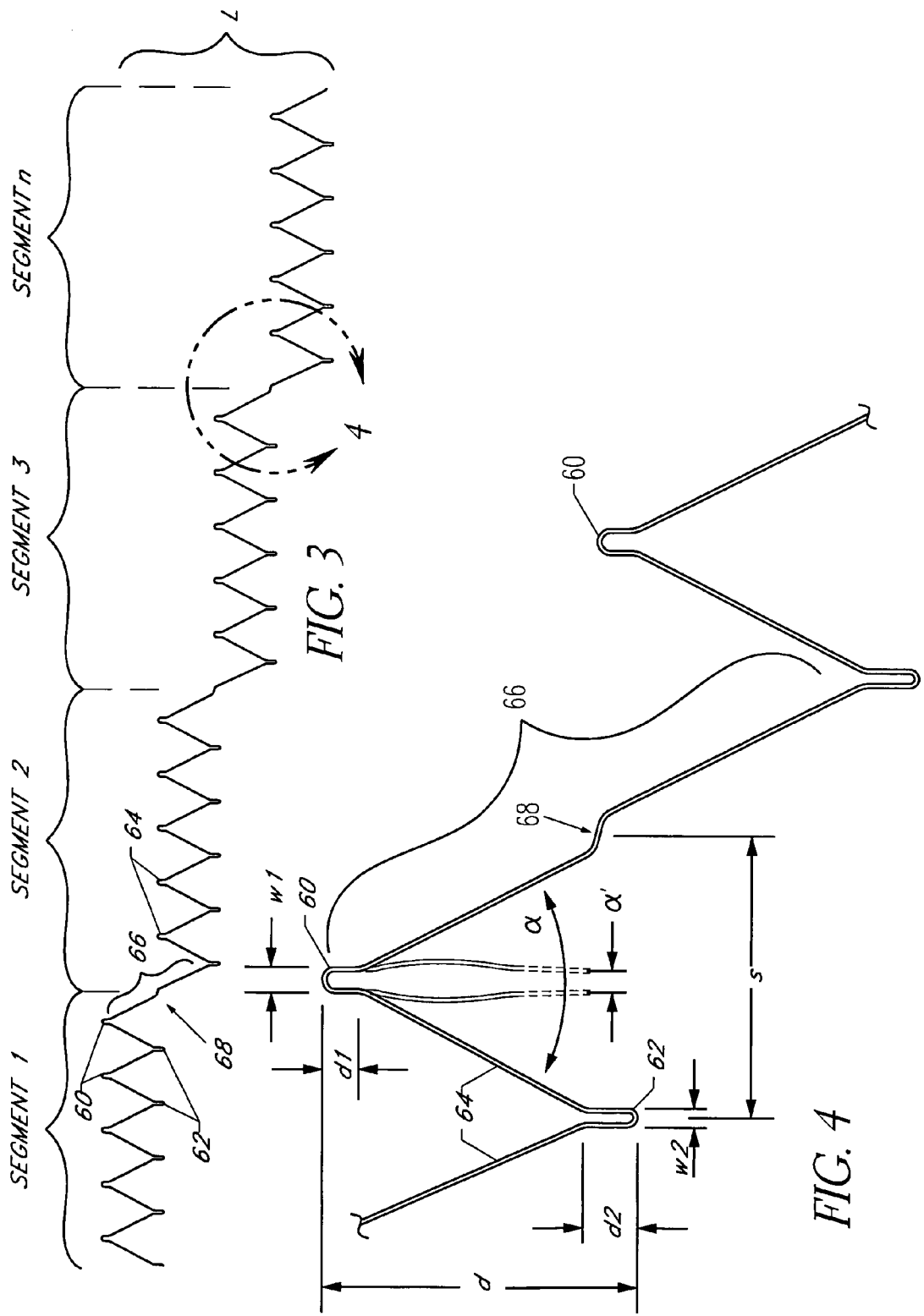

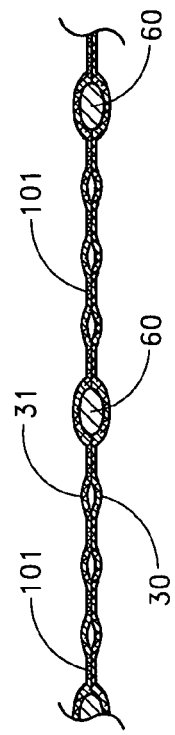
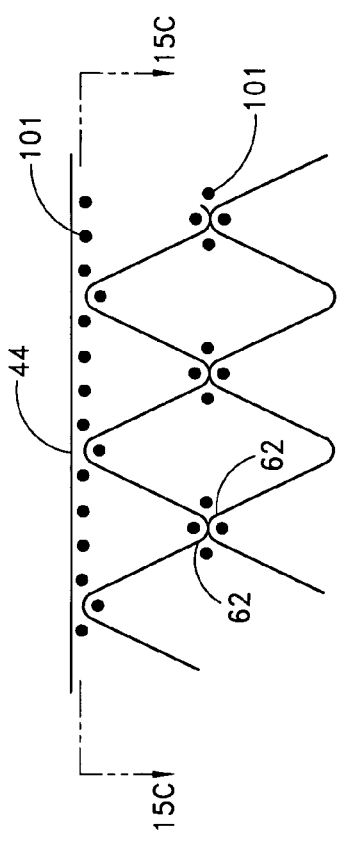
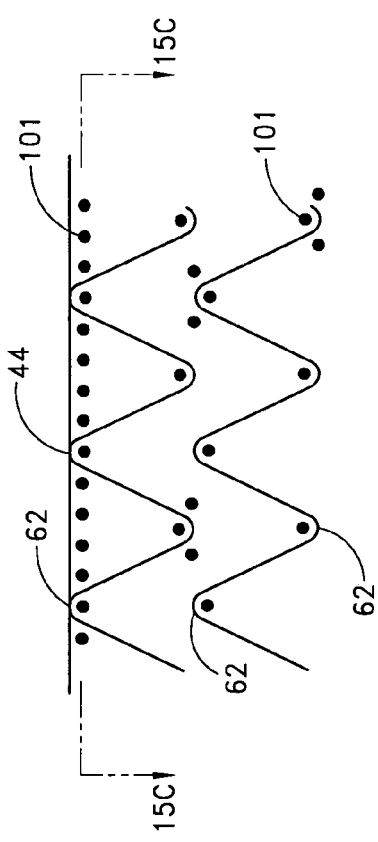
FIG. 15A
FIG. 15B
FIG. 15C

FIG. 16
FIG. 17
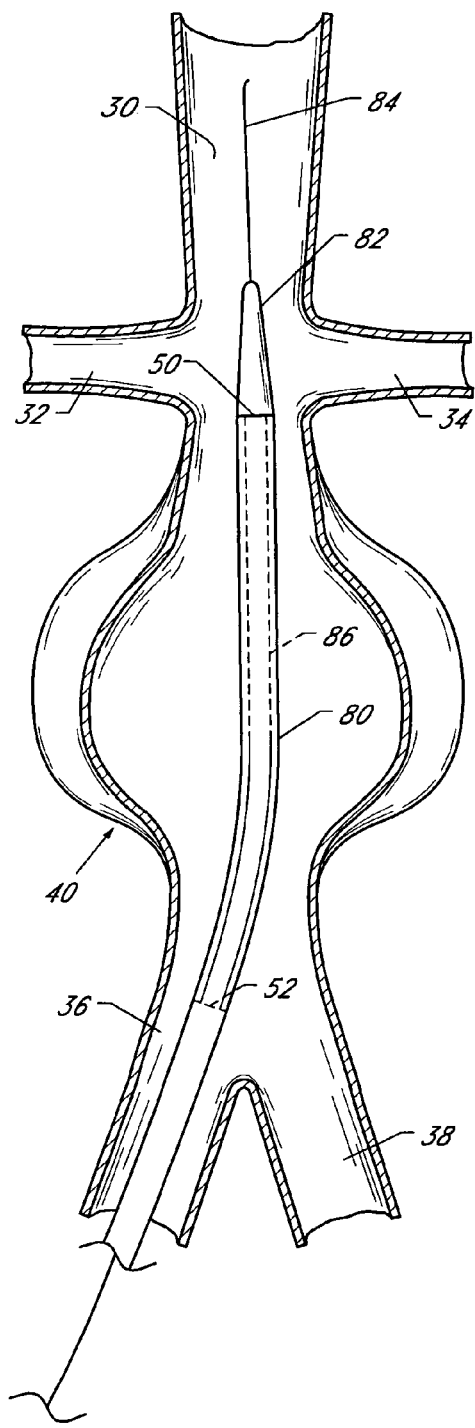
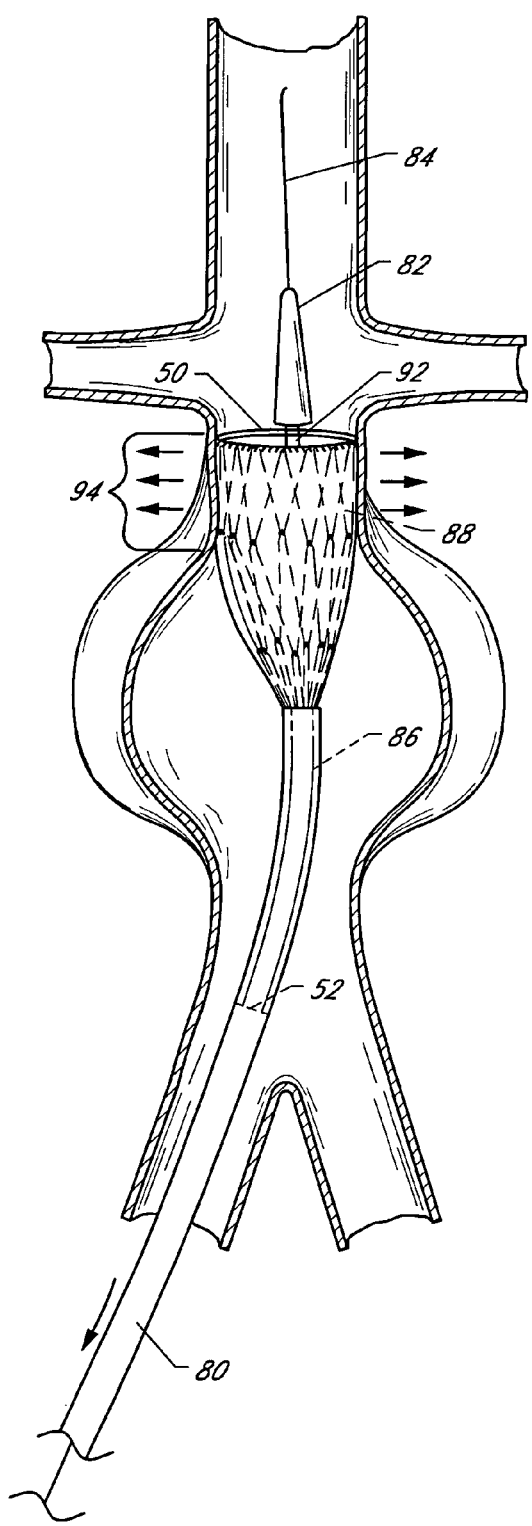

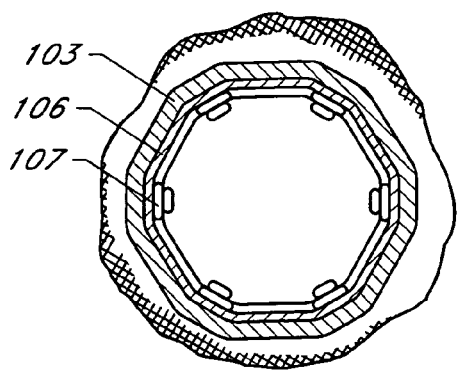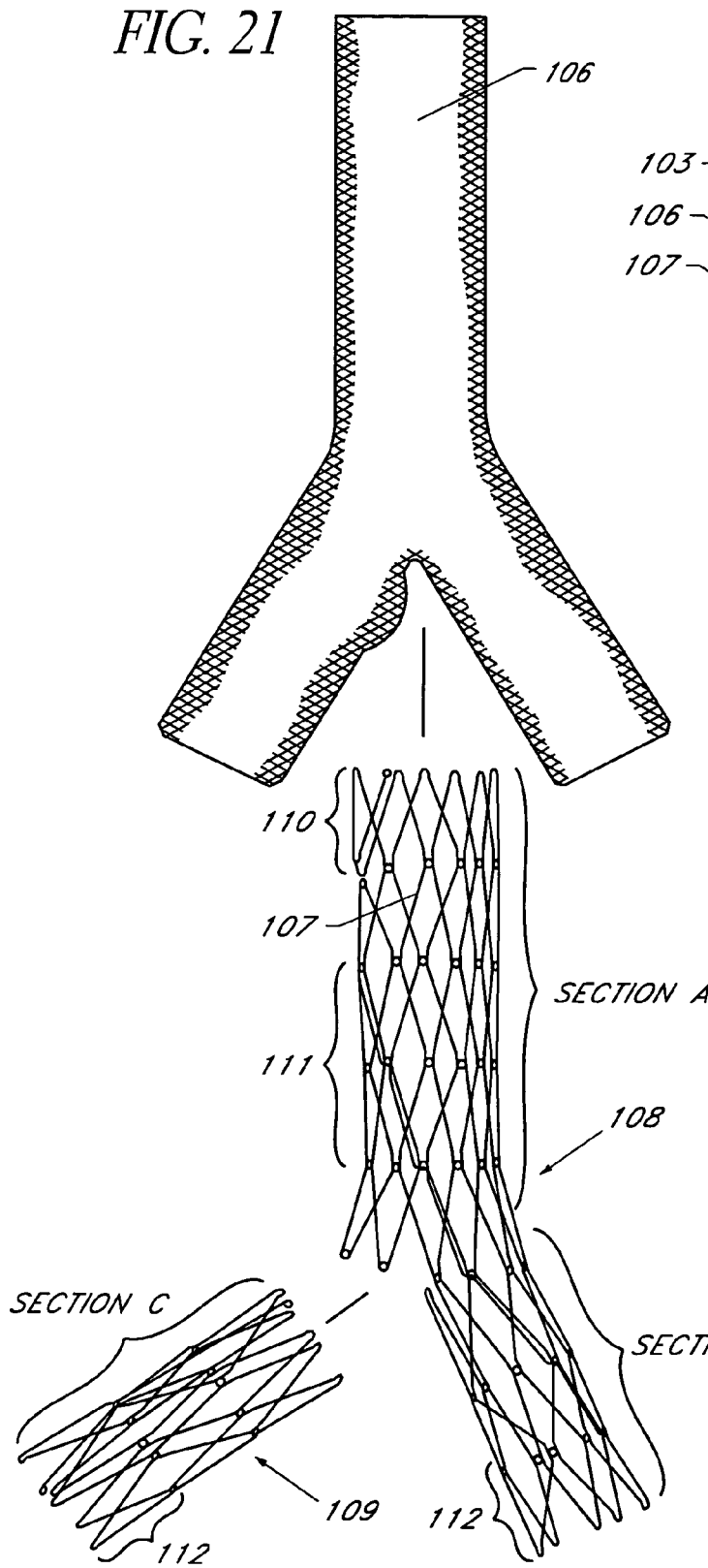

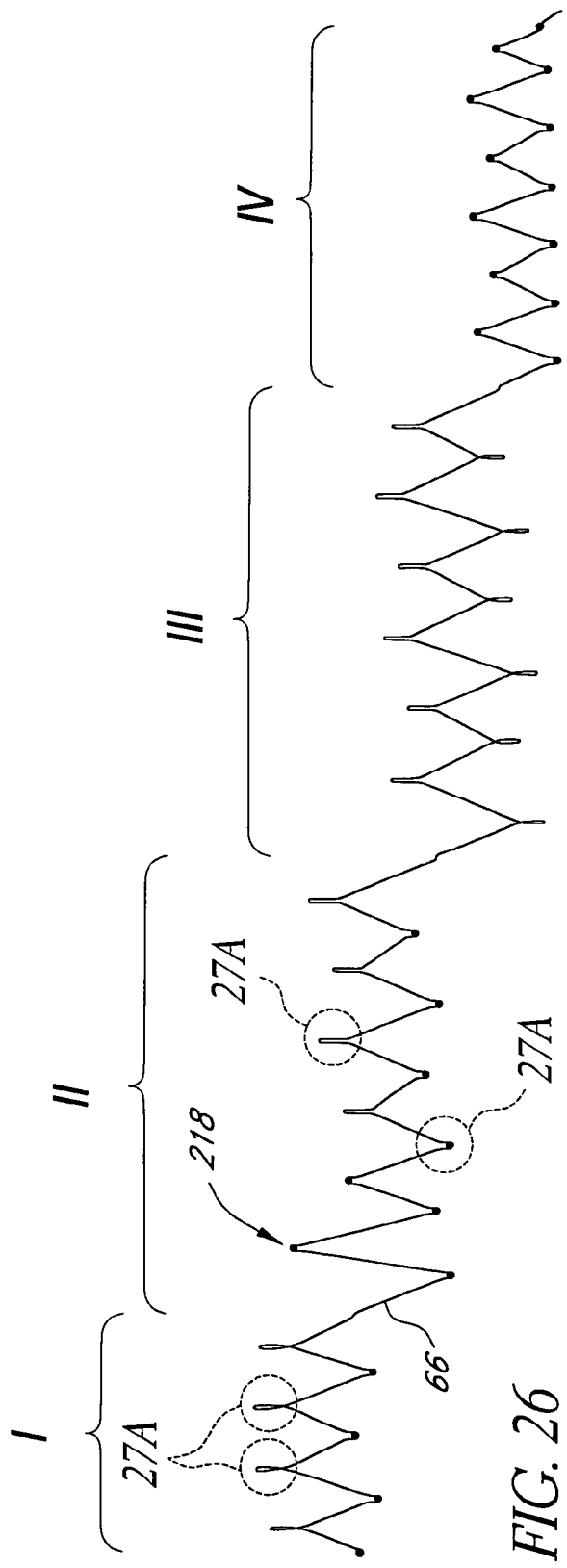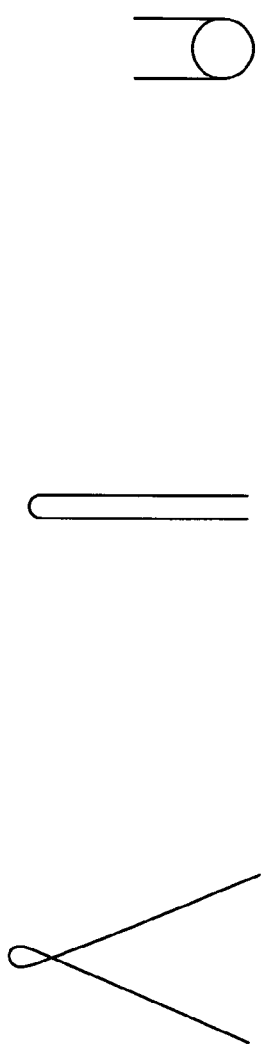

ENDOLUMENAL VASCULAR PROSTHESIS WITH NEOINTIMA INHIBITING POLYMERIC SLEEVE

BACKGROUND OF THE INVENTION

1. Field of the Invention

The present invention relates to an endolumenal vascular prosthesis, and in particular, to a self-expanding low profile prosthesis for use in the treatment of abdominal aortic aneurysms. An ePTFE membrane on the prosthesis exhibits physical properties which inhibit the formation of a thin viable neointima through the membrane.

2. Description of the Related Art

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, e.g., below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of Polyester, Urethane, DACRON®, TEFLON®, or other suitable material.

To perform the surgical procedure requires exposure of the aorta through an abdominal incision which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON® tube, or graft, of approximately the same size as the normal aorta is sutured in place, thereby replacing the aneurysm. Blood flow is then re-established through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include: the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. The graft must be secured, or sutured, to the remaining portion of the aorta, which may be difficult to perform because of the thrombosis present on the remaining portion of the aorta. Moreover, the remaining portion of the aorta wall is frequently friable, or easily crumbled.

Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. J. C. Parodi et al., Transfemoral Intraluminal Graft Implantation for Abdominal Aortic Aneurysms, 5 Annals Vascular Surgery 491 (1991). Endovascular grafting involves the translumenal placement of a prosthetic arterial graft within the lumen of the artery.

In general, transluminally implantable prostheses adapted for use in the abdominal aorta comprise a tubular wire cage surrounded by a tubular sleeve made of polytetrafluoroethylene (PTFE) or Dacron®. Both balloon expandable and self expandable support structures have been proposed. Endovascular grafts adapted to treat both straight segment and bifurcation aneurysms have also been proposed.

Notwithstanding the foregoing, there remains a need for a structurally simple, easily deployable endovascular prosthesis having a low profile adapted for translumenal delivery. Moreover, this need extends to prosthesis adaptable to span either a straight or bifurcated abdominal aortic aneurysm. Preferably, the tubular prosthesis can be self expanded at the site to treat the abdominal aortic aneurysm, and exhibits flexibility to accommodate nonlinear anatomies and normal anatomical movement.

SUMMARY OF THE INVENTION

The present invention provides a tubular prosthesis for spanning a defect in the vascular system, such as an abdominal aortic aneurysm. The prosthesis comprises a support frame, and an expanded polytetrafluoroethylene (ePTFE) membrane thereon. The physical properties of the ePTFE membrane have been optimized to enable the prosthesis to isolate the aneurysmic sack while at the same time preventing tissue ingrowth through the wall sufficient to form and nourish a thin viable neointimal layer along the inside surface of the prosthesis. Due to the interplay of the wall thickness, density, intranodal distance, and possibly other physical characteristics of the ePTFE, the neointima inhibiting ePTFE liner in accordance with the present invention cannot be described in terms of a specific set of variables. To the contrary, changes in any one variable may be offsetable by commensurate changes in another variable, to produce a neointima inhibiting ePTFE in accordance with the present invention. Such optimization can be accomplished through routine experimentation by those of skill in the art in view of the disclosure herein, and in view of the objective of inhibiting the formation of a viable neointima on the lumenal side of the ePTFE membrane, nourished through the membrane.

In accordance with one aspect of the present invention, there is provided a prosthetic vascular graft. The graft comprises an expandable tubular support, and a tubular ePTFE layer carried by the support. The ePTFE layer comprises a wall thickness of less than about 0.15 mm, an average density of greater than about 0.75 gm/ml, and an average distance between nodes in the range of between about 6 to about 80 microns. The ePTFE layer prevents the formation and nourishment of a viable neointimal layer therethrough.

There is provided in accordance with another aspect of the present invention, a method of treating a patient. The method comprises the steps of providing an implantable tubular prosthesis, having an ePTFE layer thereon. The prosthesis is positioned across a defect in a vessel, such that a first side of the layer is in contact with the wall of the vessel. Formation of a viable neointima on a second side of the layer, nourished through the layer is inhibited, by providing the ePTFE layer with a density of greater than about 0.75 gm/ml and a wall thickness of less than 0.2 mm.

In accordance with a further aspect of the present invention, there is provided an endolumenal prosthesis having a lumenal surface and an ablumenal surface. The prosthesis comprises a tubular wire support with proximal and distal ends and a central lumen extending therebetween. The wire support comprises at least two axially adjacent tubular segments, each segment comprising a series of proximal and distal bends connected by a length of wire. The wire support is radially compressible into a first, reduced cross-sectional configuration for translumenal navigation to a treatment site in a body lumen, and self expandable to a second, enlarged cross-sectional configuration for deployment at the treatment site in the body lumen.

A tubular ePTFE sheath is provided on the wire support, the sheath being configured to inhibit the formation of a viable neointimal layer on the lumenal surface of the sheath.

The ePTFE sheath generally has a wall thickness of no greater than about 0.2 mm, and often has a wall thickness within the range of from about 0.05 mm to about 0.15 mm. In one embodiment, the ePTFE sheath has a wall thickness of about 0.1 mm.

The ePTFE sheath generally has a density of at least about 0.5 gm/ml. In certain embodiments, the ePTFE sheath has a density of at least about 0.75 gm/ml, and the ePTFE sheath in certain embodiments has a density within the range of from 1.1 gm/ml to about 1.5 gm/mm.

The ePTFE sheath has a plurality of nodes and the average distance between nodes is generally within the range of from about 6 microns to about 80 microns.

In accordance with a further aspect of the present invention, there is provided a prosthetic vascular structure. The structure comprises expanded polytetrafluoroethylene, the expanded polytetrafluoroethylene further comprising a macroscopically tubular configuration with a proximal end, a distal end and an inner surface, and a microscopic superstructure of irregularly spaced nodes of various sizes and shapes interconnected by fibrils.

The vascular structure further comprises an average wall thickness of less than about 0.2 mm, and a substantially uniform distribution of nodes throughout the tubular configuration.

The vascular structure additionally comprises an average density of greater than about 0.5 gm/ml. The structure is configured to provide for the smooth flow of blood between at least two points in a living organism, while controlling cellular ingrowth through the wall of the tubular configuration to substantially prevent the formation of a thin, viable neointima over the inner surface thereof.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 3 is a plan view of a formed wire useful for rolling about an axis into a multi-segment support structure in accordance with the present invention.

FIG. 4 is an enlarged detail view of a portion of the formed wire illustrated in FIG. 3.

FIGS. 15A and 15B are schematic views of a portion of a wall of a graft, laid out flat, illustrating two alternative wire support configurations having spot welds between lumenal and exterior layers of a polymeric membrane.

FIG. 15C is a cross-sectional view through the wall taken along line C-C in FIGS. 15A and 15B.

FIG. 16 is a schematic illustration of a straight segment delivery catheter in accordance with the present invention, positioned within an abdominal aortic aneurysm.

FIG. 17 is an illustration as in FIG. 16, with the straight segment endolumenal prosthesis partially deployed from the delivery catheter.

FIG. 21 is an exploded view of the implanted graft of FIG. 20.

FIG. 22 is a cross sectional view of the bifurcated vascular prosthesis in accordance with the present invention, taken along the line 22-22 of FIG. 20.

FIG. 26 is a plan view of formed wire useful to form a branch support structure in accordance with the three-part support embodiment of the present invention shown in FIG. 24.

FIGS. 27A, 27B and 27C are enlargements of the apexes delineated by lines A, B and C, respectively, in FIG. 26.

DETAILED DESCRIPTION OF THE EMBODIMENTS

Figure 1:
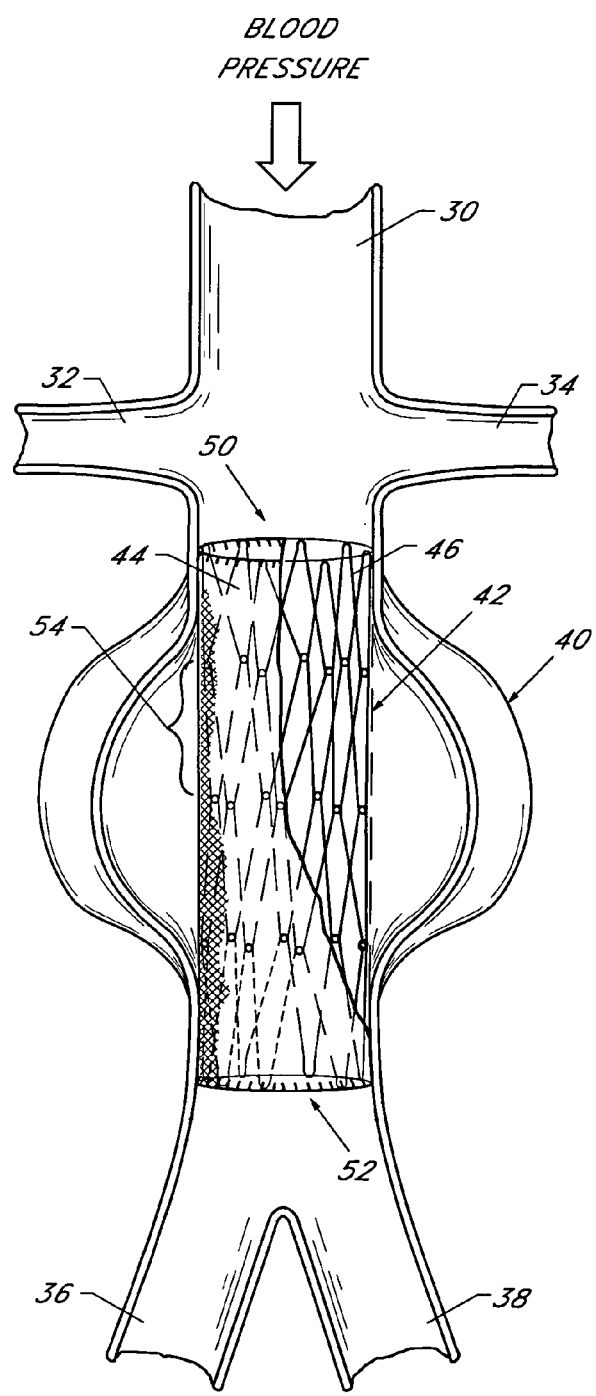
FIG. 1 is a schematic representation of a straight segment vascular prosthesis in accordance with the present invention, positioned within a symmetric abdominal aortic aneurysm.

Referring to FIG. 1, there is disclosed a schematic representation of the abdominal part of the aorta and its principal branches. In particular, the abdominal aorta 30 is characterized by a right renal artery 32 and left renal artery 34. The large terminal branches of the aorta are the right and left common iliac arteries 36 and 38. Additional vessels (e.g., second lumbar, testicular, inferior mesenteric, middle sacral) have been omitted for simplification. A generally symmetrical aneurysm 40 is illustrated in the infrarenal portion of the diseased aorta. An expanded straight segment endolumenal vascular prosthesis 42, in accordance with one embodiment of the present invention, is illustrated spanning the aneurysm 40.

The endolumenal vascular prosthesis 42 includes a polymeric sleeve 44 and a tubular wire support 46, which are illustrated in situ in FIG. 1. The sleeve 44 and wire support 46 are more readily visualized in the exploded view shown in FIG. 2. The endolumenal prosthesis 42 illustrated and described herein depicts an embodiment in which the polymeric sleeve 44 is situated concentrically outside of the tubular wire support 46. However, other embodiments may include a sleeve 44 or sleeves 44 situated substantially support 46. Alternatively, the wire support 46 may be embedded within a polymeric matrix which makes up the sleeve 44. Regardless of whether the sleeve 44 is inside or outside the wire support 46, or both inside and outside, the sleeve 44 may be attached to the wire support 46 by any of a variety of methods or devices, including laser bonding, adhesives, clips, sutures, lamination, dipping or spraying or others, depending upon the composition of the sleeve or membrane 44 and overall prosthesis design.

In one embodiment, the tubular wire support 46 is formed from a continuous single length of round or flattened wire. As used herein, "wire" includes its ordinary meaning, conventional wire, as well as filaments having rectangular or other cross sections formed by laser cutting or otherwise etching a support structure from a sheet or tube stock. Alternatively, two or more wire lengths can be secured together to produce the wire support 46. The wire support 46 is preferably formed in a plurality of discrete tubular segments 54, connected together and oriented about a common axis. Each pair of adjacent segments 54 may be connected by a connector 66 as illustrated in FIG. 3. The connectors 66 collectively produce a generally axially extending backbone which adds axial strength to the prosthesis 42. Adjacent segments can be connected both by the backbone, as well as the interlocking junction disclosed below. Additional structures, including circumferentially extending sutures, solder joints, and wire loops may also be used. Alternatively, in one embodiment, adjacent wire cage segments may be held together by the polymeric sleeve in which the cage is embedded. This embodiment is detailed below.

The segmented configuration of the tubular wire support 46 facilitates a great deal of flexibility. Each segment 54, though joined to adjacent segments, may be independently engineered to yield desired parameters. Each segment may range in axial length from about 0.3 to about 5 cm or longer for certain applications. Generally, the shorter the segment's length the greater its radial strength. An endolumenal prosthesis may include from about 1 to about 50 segments, preferably from about 3 to about 10 segments. For example, while a short graft patch, in accordance with the invention, may comprise only 2 segments and span a total of 2 to 3 cm, a complete graft may comprise 4 or more segments and span the entire aortic aneurysm. In addition to the flexibility and other functional benefits available through employment of different length segments, further flexibility can be achieved through adjustments in the number, angle, or configuration of the wire bends associated with the tubular support.

In addition to having differing expanded diameters in different zones of the prosthesis 42, different zones can be provided with a different radial expansion force, such as ranging from about 0.2 lbs to about 0.8 lbs. In one embodiment, the proximal zone 55 is provided with a greater radial force than the central zone 57 and/or distal zone 59. The greater radial force can be provided in any of a variety of manners discussed elsewhere herein, such as through the use of an additional one or two or three or more proximal bends 60, distal bends 62 and wall sections 64 compared to a reference segment 54 in the central zone 57 or distal zone 59. Alternatively, additional spring force can be achieved in the proximal zone 55 through the use of the same number of proximal bends 60 as in the rest of the prosthesis, but with a heavier gauge wire.

The wire may be made from any of a variety of different materials, such as elgiloy, Nitinol or MP35N, or other alloys which include nickel, titanium, tantalum, or stainless steel, high Co—Cr alloys or other temperature sensitive materials. For example, an alloy comprising Ni 15%, Co 40%, Cr 20%, Mo 7% and balance Fe may be used. The tensile strength of suitable wire is generally above about 300 Ksi and often between about 300 and about 340 Ksi for many embodiments. In one embodiment, a Chromium-Nickel-Molybdenum alloy such as that marketed under the name Conichrom (Fort Wayne Metals, Indiana) has a tensile strength ranging from 300 to 320 K psi, elongation of 3.5-4.0%. The wire may be treated with a plasma coating and be provided with or without additional coatings such as PTFE, Teflon, Perlyne and drugs.

In addition to segment length and bend configuration, discussed above, another determinant of radial strength is wire gauge. The radial strength, measured at 50% of the collapsed profile, preferably ranges from about 0.2 lb to 0.8 lb, and generally from about 0.4 lb to about 0.5 lb or more. Preferred wire diameters in accordance with the present invention range from about 0.004 inches to about 0.020 inches. More preferably, the wire diameters range from about 0.006 inches to about 0.018 inches. In general, the greater the wire diameter, the greater the radial strength for a given wire layout. Thus, the wire gauge can be varied depending upon the application of the finished graft, in combination with/or separate from variation in other design parameters (such as the number of struts, or proximal bends 60 and distal bends 62 per segment), as will be discussed. A wire diameter of approximately 0.018 inches may be useful in a graft having four segments each having 2.5 cm length per segment, each segment having six struts intended for use in the aorta, while a smaller diameter such as 0.006 inches may be useful for a 0.5 cm segment graft having 5 struts per segment intended for the iliac artery. In one embodiment, the length of vascular prosthesis 42 is about 28 cm.

In one embodiment of the present invention, the wire diameter is tapered from the proximal to distal ends. Alternatively, the wire diameter may be tapered incrementally or stepped down, or stepped up, depending upon differing radial strength requirements along the length of the graft for each particular clinical application. In one embodiment, intended for the abdominal aortic artery, the wire has a cross-section of about 0.018 inches in the proximal zone 55 and the wire tapers down to a diameter of about 0.006 inches in the distal zone 59 of the graft 42. End point dimensions and rates of taper can be varied widely, within the spirit of the present invention, depending upon the desired clinical performance.

The polymeric sleeve in accordance with the present invention is illustrated, for example, in FIGS. 2, 20, 21 and 28. Polymeric sleeve 44 is illustrated as a substantially cylindrical tube of polymeric material, but may be manufactured in a variety of shapes and sizes, as is well known to those of skill in the art. For example, in one application, polymeric sleeve 44 is configured for use at a bifurcation within the human body's vasculature, such as polymeric sleeve 106 of FIGS. 20 and 21 described below. In other embodiments, the polymeric sleeve 44 described below may be used without a wire support or a wire support formed in a manner not described herein.

Figure 28:
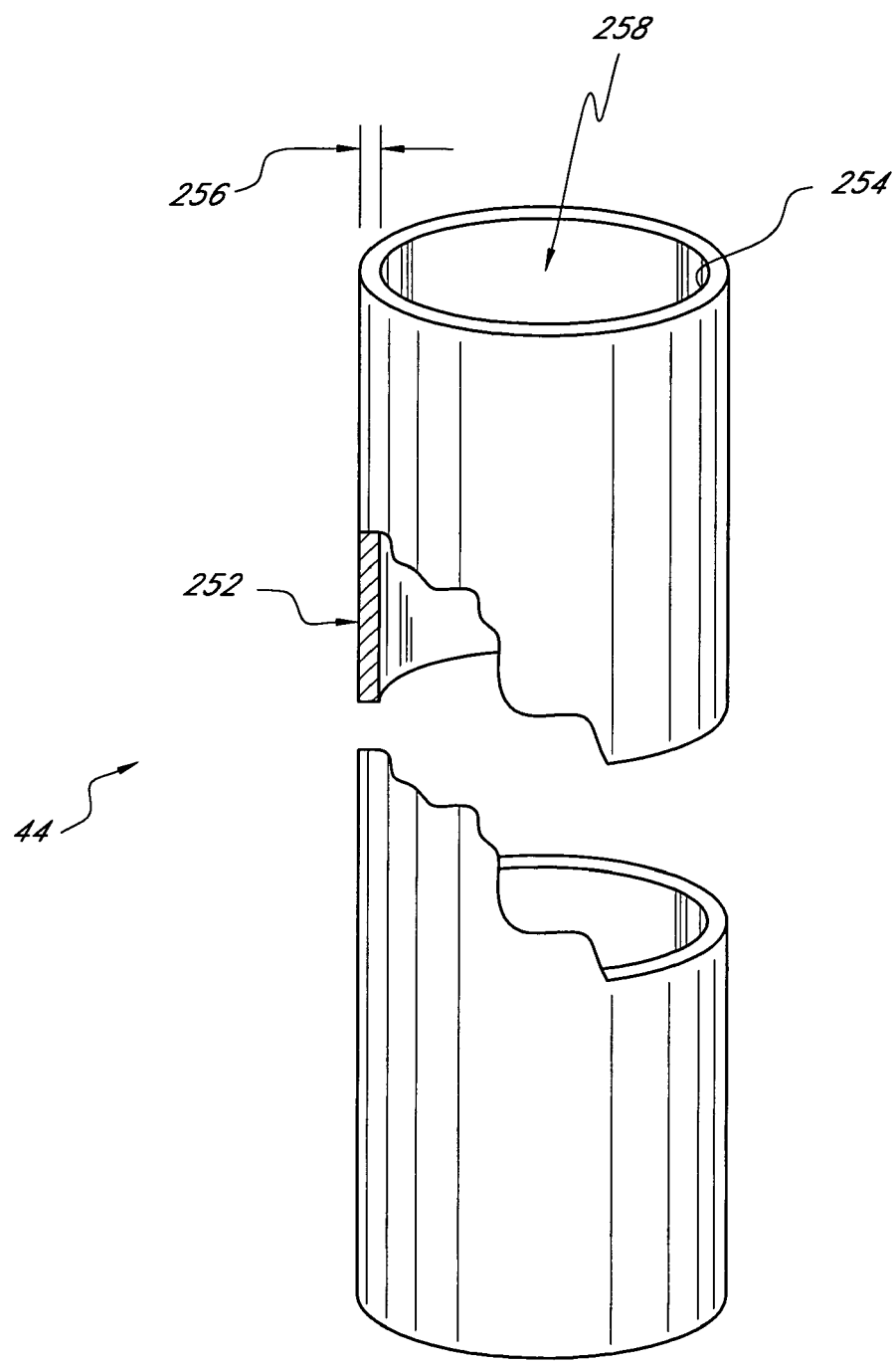
FIG. 28 is a schematic representation of a polymeric sleeve in accordance with one embodiment of the present invention.

Referring to FIG. 28, polymeric sleeve 44 includes an outer, or ablumenal surface 252, an inner or lumenal surface 254, and a wall thickness 256 therebetween. The inner surface 254 defines a lumen 258 through which bodily fluid, such as blood, may flow. As mentioned above, the polymeric sleeve 44 is adapted to be used as a graft, without a support frame (as shown in FIG. 28), or may be used in conjunction with a frame, such as described in greater detail herein (e.g., wire cage 46 of FIGS. 1, 2 and 19, or wire support 107 of FIG. 20).

In one embodiment, the polymeric sleeve 44 is placed over at least a portion of a frame such that the inner surface 254 of the polymeric sleeve 44 is adjacent the outer surface of the frame, the polymeric sleeve 44 acting as a frame cover. In another embodiment, the polymeric sleeve 44 is placed inside at least a portion of a frame such that the outer surface 252 of the polymeric sleeve 44 is adjacent the inner surface of the frame, the polymeric sleeve 44 acting as a frame liner. In another embodiment, the frame is embedded or encapsulated between at least two polymeric sleeves 44, as described elsewhere herein. An adhesive bonding layer (not shown) may be used to adhere the polymeric sleeve 44 to the frame, or to another polymeric sleeve 44. Other adhesive methods, such as sintering or laser welding, may alternatively be used, as described below.

Figure 29:
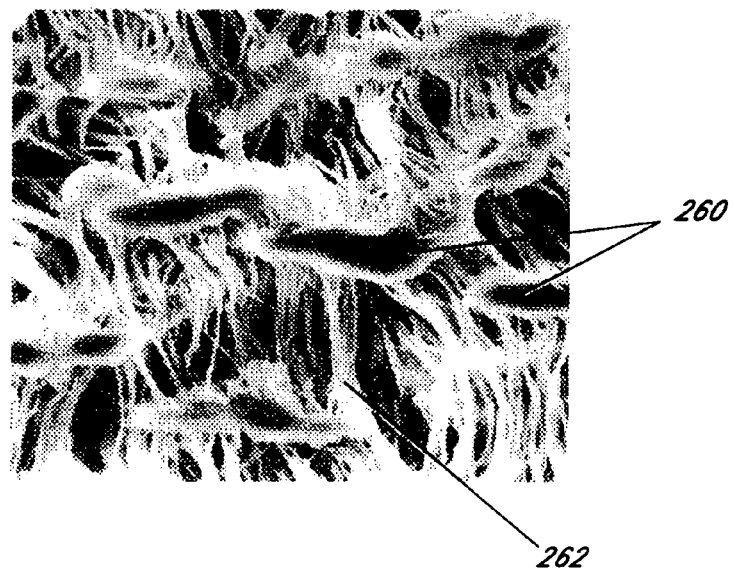
FIG. 29 is a 1000× magnified view of a portion of the polymeric sleeve of FIG. 28.

The polymeric sleeve 44 generally has a microscopic superstructure of uniformly distributed nodes which are interconnected by fibrils. The node-fibril superstructure of ePTFE is generally well understood by those of skill in the art. One example of prior art ePTFE is illustrated at approximately 1000× magnification in FIG. 29. The nodes 260 of ePTFE are generally longitudinally aligned and extend along an axis transverse to the axis of expansion of the ePTFE. The fibrils 262 of ePTFE span between the nodes 260, and are generally longitudinally aligned and extend along an axis parallel to the axis of expansion of the ePTFE.

In addition, the polymeric sleeve 44 may be characterized by its wall thickness 256 (as illustrated in FIG. 28), an average internodular distance (not shown), and an average density (not shown). When these characteristics are properly selected, and unlike prior art ePTFE sleeves, such as, for example, that disclosed in U.S. Pat. No. 6,436,135, the polymeric sleeve 44 of the present invention will prohibit the formation of a viable neointimal layer through the wall of the sleeve and along the sleeve's inner surface 254.

The term "neointimal layer" includes its ordinary meaning, as is known to those of skill in the art, as well as a thin lining of viable endothelial cells that would typically be less than ten blood-cells thick. A neointimal layer is one that generally forms along the inner surface of a medical device, such as the prosthetic vascular structure taught by Goldfarb in U.S. Pat. No. 6,436,145, incorporated by reference herein. The "neointima" is similar to the inner surface of natural blood vessels, known to those of skill in the art as the "intima." The intima is generally characterized by a thin, delicate layer of endothelial cells whose function is to provide a smooth interface between the blood stream and the vessel wall. The natural intima serves to lessen the severity of irregular vessel wall transitions, thereby helping to assure laminar blood flow.

However, it has been found clinically useful in certain settings to prevent the formation of a neointimal layer over the inner surface of a prosthetic structure, such as a polymeric sleeve 44. Preventing the formation of a neointimal layer may have the benefit of reducing the risk of excessive overgrowth, hyperplasia, and occlusion of the vessel and other clinically adverse events.

An ePTFE sleeve 44 in accordance with the present invention generally will have a wall thickness 256 less than about 0.2 mm, often no greater than about 0.15 mm or 0.125 mm, and in one embodiment about 0.11 mm. The internodal distance is generally in the range of between about 5 and about 100 μm, often in the range of between about 10 and 50 μm, and in one embodiment is in the range of between about 25 and 40 μm. The average density is generally greater than about 0.5 g/ml, often in excess of about 0.75 g/ml, and depending upon other variables, is at least about 1.0 or at least about 1.2. In one embodiment the average density is in the range of about 1.0 g/ml to about 1.5 g/ml, and it generally is no greater than about 2 g/ml.

The foregoing characteristics can be optimized in view of each other to achieve a polymeric sleeve 44 that can function in the abdominal aortic aneurysm environment to isolate the aneurysmic sac while at the same time preventing tissue ingrowth through the wall in the landing zones of the sleeve 44. The landing zones include the locations generally in the proximal and distal end region of the sleeve 44 where it is in contact with native healthy intima of the vessel in which it is inserted.

Although the foregoing physical properties provide guidance to the selection of a specific ePTFE material, one or more of the characteristics described above may be selected outside the ranges provided, and the sleeve 44 may still be capable of preventing the formation and sustaining of a viable neointimal layer as long as the other characteristics are selected to compensate. For example, a wall thickness outside of the foregoing ranges will not necessarily cause the sleeve 44 to allow the formation of a neointimal layer as long as the density or one or more other characteristics is properly selected. Routine experimentation, as well as the methods taught by Goldfarb in U.S. Pat. No. 6,436,145, incorporated by reference herein, may be used to optimize the sleeve 44 characteristics in order to prevent neointima formation for any given combination of selected sleeve 44 characteristics.

In another embodiment of the present invention a neointima inhibiting polymeric sleeve is formed by treating or coating a sleeve, such as a sleeve which would otherwise have allowed the formation of a neointima, with a sealant. Neointima forming sleeves are well known in the art. Examples of such sleeves are taught by Goldfarb in U.S. Pat. No. 6,436,145. The sealant provides a mechanical and/or chemical barrier to the migration of cells through the polymeric sleeve 44 wall, thereby preventing the formation of a neointimal layer on the luminal side of the sleeve's 44 wall.

In another embodiment, a coating having controlled cytotoxicity is applied to a sleeve 44. The coating prevents the migration of cells through the polymeric sleeve 44. wall, yet is not sufficiently cytotoxic to cause clinically adverse events.

Neointima inhibiting polymeric sleeves 44 in accordance with the present invention may upon explantation exhibit a structured thrombus formation, or fibrin coating, or other proteinaceous layer along the inner surface 254 thereof. However, these formations are not a viable neointimal layer as contemplated herein, such as a thin, viable neointima which is nourished through the sleeve 44 wall thickness 256. A thin, partial neointimal layer may also be observed upon explantation to have climbed around the ends of the sleeve 44 and adhere to the inner surface of the sleeve 44 for a short distance from its ends. However, this growth also is not a viable neointimal layer which is nourished through the sleeve 44 wall thickness 256.

Polymeric sleeves 44 within the contemplation of the present invention may also allow partial tissue ingrowth into the polymeric sleeve 44 wall thickness 256. Such partial tissue ingrowth may be advantageous for anchoring of the polymeric sleeve 44 within the body lumen. But the ePTFE sleeves within the present invention inhibit further growth such as would support the formation of a neointimal layer over the polymeric sleeve 44 inner surface 254. The cross-sectional view of one such neointimal layer-inhibiting polymeric sleeve 44 is schematically illustrated in FIG. 30

Figure 30:
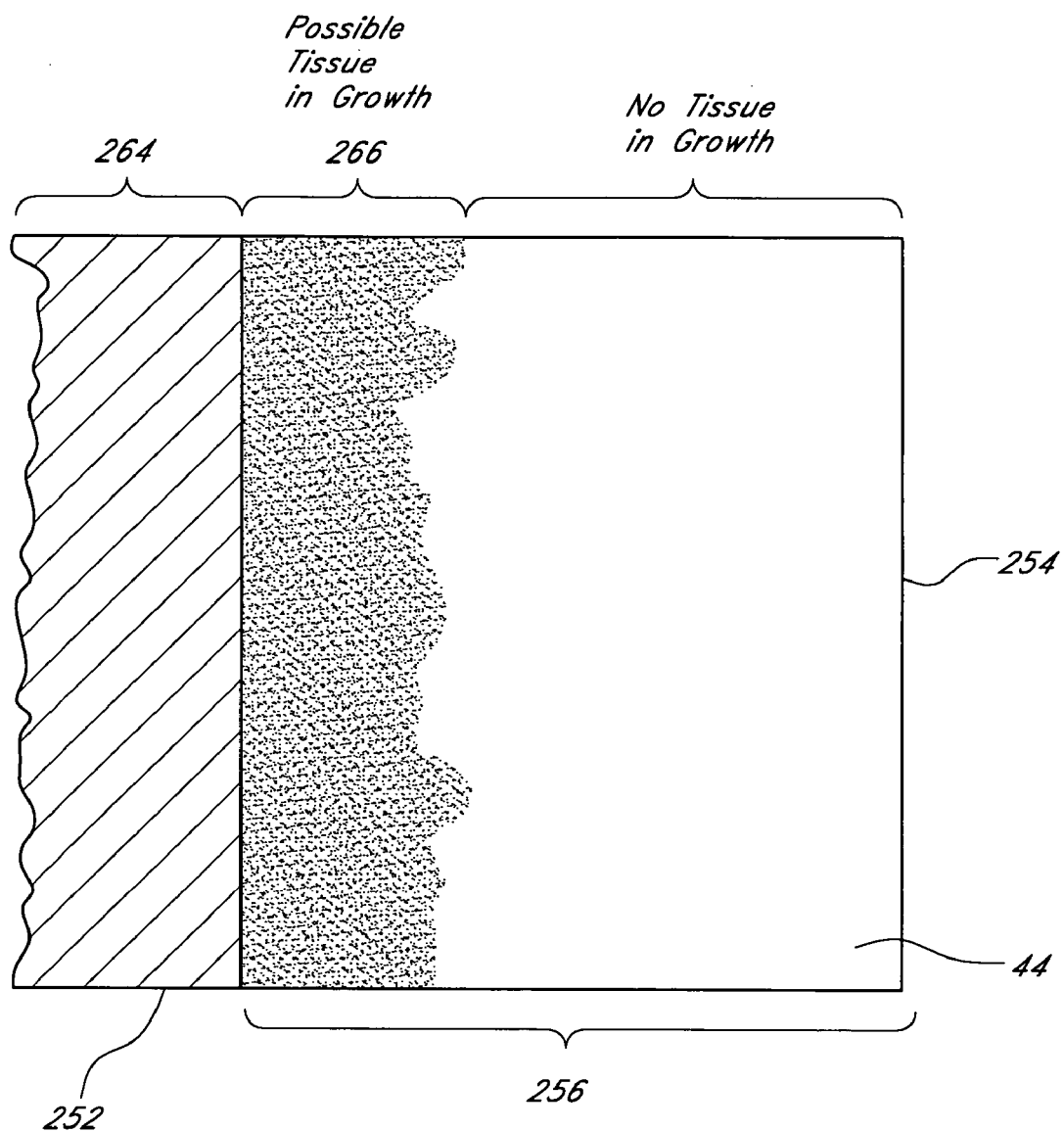
FIG. 30 is a cross-sectional view of a segment of a polymeric sleeve after having been explanted from a medical patient.

The polymeric sleeve 44 of FIG. 30 schematically represents the expected finding in an abdominal aortic aneurysm bifurcation graft explanted from a human recipient post mortem after an implantation period of six months. A uniform, firmly attached encapsulation of collagenous matter 264 is shown covering the outer surface 252 of the polymeric sleeve 44. Some tissue ingrowth 266 may have occurred into a portion (e.g., approximately 40%) of the wall thickness 256 of the polymeric sleeve 44. However, any tissue ingrowth 266 is not sufficient to establish the formation of a viable, neointimal layer over the inner surface 254 of the polymeric sleeve 44. As shown in FIG. 30, the polymeric sleeve 44 prohibits the formation of a viable neointimal layer. Thrombus formation and/or a fibrin coating may be present on the inner (lumenal) surface 254 of tubular sleeve 44.

In one embodiment, the material of the polymeric sleeve 44 is expanded polytetrafluoroethylene (ePTFE). The process of expanding polytetrafluoroethylene (PTFE) is well known to those of skill in the art. In general, to expand PTFE, a resin is extruded into a desired geometrical configuration, such as a sheet. As the extrudate is stretched, the non-porous PTFE separates into solid nodes of PTFE which are structurally interconnected by PTFE fibrils. The fibrils are drawn from the nodes during expansion.

The extrudate is heated at a temperature below the sintering temperature, which in one embodiment is 327° C., and then physically stretched or expanded along at least one direction. The expanded material is then restrained against contraction, and is sintered by brief exposure to temperatures in excess of the sintering temperature. Sintering causes crystallization of the expanded structure, and increased tensile strength of up to about 6500 psi.

The nodes are roughly ellipsoidal in shape, and are of random, but generally uniform size, and are distributed in a homogeneous pattern throughout the wall thickness 256. In addition, in one embodiment, the nodes are typically less than a few times the size of a normal fibroblast or red blood cell. Additional details of the ePTFE production process are well known to those of skill in the art. One example of such process is disclosed in U.S. Pat. No. 4,187,390, which is incorporated in its entirety by reference herein. Post processing steps such as compression to increase density and/or reduce wall thickness may also be used.

The foregoing neointima inhibiting material may be used in any of a variety of applications, such as for the tubular fabric liner of a self expandable graft as is discussed below. Referring to FIG. 3, there is illustrated a plan view of a single formed wire used for rolling about a longitudinal axis to produce a four segment straight tubular wire support. The formed wire exhibits distinct segments, each corresponding to an individual tubular segment 54 in the tubular support 46 (see FIGS. 1 and 2).

Each segment 54 has a repeating pattern of proximal bends 60 connected to corresponding distal bends 62 by wall sections 64 which extend in a generally zig-zag configuration when the segment 54 is radially expanded. Each segment 54 is connected to the adjacent segment 54 through a connector 66, except at the terminal ends of the graft. The connector 66 in the illustrated embodiment comprises two wall or strut sections 64 which connect a proximal bend 60 on a first segment 54 with a distal bend 62 on a second, adjacent segment 54. The connector 66 may additionally be provided with a connector bend 68, which may be used to impart increased radial strength to the graft and/or provide a tie site for a circumferentially extending suture.

Referring to FIG. 4, there is shown an enlarged view of the wire support illustrating a connector 66 portion between adjacent segments 54. In the embodiment shown in FIG. 4, a proximal bend 60 comprises about a 180 degree arc, having a radial diameter w1, which in one embodiment ranges from 0.070 to 0.009 inches depending upon the wire diameter. The proximal bend 60 is followed by a relatively short length of parallel wire that spans an axial distance d1. The parallel wires thereafter diverge outwardly from one another and form the strut sections 64, or the proximal half of a connector 66. At the distal end of the strut sections 64, the wire forms a distal bend 62, preferably having identical characteristics as the proximal bend 60, except being concave in the opposite direction. The axial direction component of the distance between the apexes of the corresponding proximal and distal bends 60, 62 on a given strut section 64 is referred to as (d) and represents the axial length of that segment. The total expanded angle defined by the bend 60 and the divergent strut sections 64 is represented by α. Upon compression to a collapsed state, such as when the graft is within the deployment catheter, the angle α is reduced to α'. In the expanded configuration, α is generally within the range of from about 35° to about 45° for a six apex section having an axial length of about 1.5 cm or 2 cm and a diameter of about 25 mm or 28 mm. The expanded circumferential distance between any two adjacent distal bends 62 (or proximal bends 60) is defined as (s).

In general, the diameter W of each proximal bend 60 or distal bend 62 is within the range of from about 0.009 inches to about 0.070 inches depending upon the wire diameter. Diameter W is preferably as small as possible for a given wire diameter and wire characteristics. As will be appreciated by those of skill in the art, as the distance W is reduced to approach two times the cross-section of the wire, the bend 60 or 62 will exceed the elastic limit of the wire, and radial strength of the finished segment will be lost. Determination of a minimum value for W, in the context of a particular wire diameter and wire material, can be readily determined through routine experimentation by those of skill in the art.

As will be appreciated from FIGS. 3 and 4, the sum of the distances (s) in a plane transverse to the longitudinal axis of the finished graft will correspond to the circumference of the finished graft cage in that plane. For a given circumference, the number of proximal bends 60 or distal bends 62 is directly related to the distance (s) in the corresponding plane. Preferably, the finished graft in any single transverse plane will have from about 3 to about 10 (s) dimensions, preferably from about 4 to about 8 (s) dimensions and, more preferably, about 5 or 6 (s) dimensions for an aortic application. Each (s) dimension corresponds to the distance between any two adjacent bends 60-60 or 62-62 as will be apparent from the discussion herein. Each segment 54 can thus be visualized as a series of triangles extending circumferentially around the axis of the graft, defined by a proximal bend 60 and two distal bends 62 or the reverse.

In one embodiment of the type illustrated in FIG. 4, w is about 2.0 mm±1 mm for a 0.018 inch wire diameter. D1 is about 3 mm±1 mm, and d is about 20 mm±1 mm. Specific dimensions for all of the foregoing variables can be varied considerably, depending upon the desired wire configuration, in view of the disclosure herein.

In one embodiment of the present invention, the apexes of adjacent segments are joined by an integral linkage formed from the wire. The form of the linkage may vary as detailed below including various types of interlocking junctions. In other embodiments, the apexes may be joined by independent structural elements such as sutures and wire loops. In yet other embodiments, the apexes of adjacent segments may not be joined at all. Rather, the formed wire may be embedded in a polymeric membrane which acts both as the graft sleeve and as a structure to join adjacent segments. Such a design has the advantage that the profile of the stent graft may be very low, since no overlapping, interlocking or external junctions are employed to hold the wire segments together. Each of these variations is discussed below.

Figure 5:
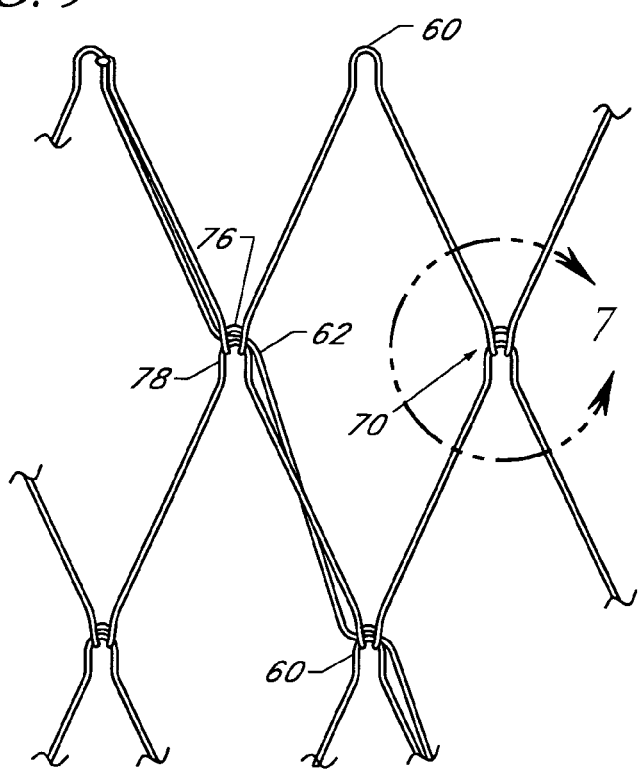
FIG. 5 is a schematic view of a portion of a wire cage wall, illustrating folded link connections between adjacent apexes.
Figure 6:
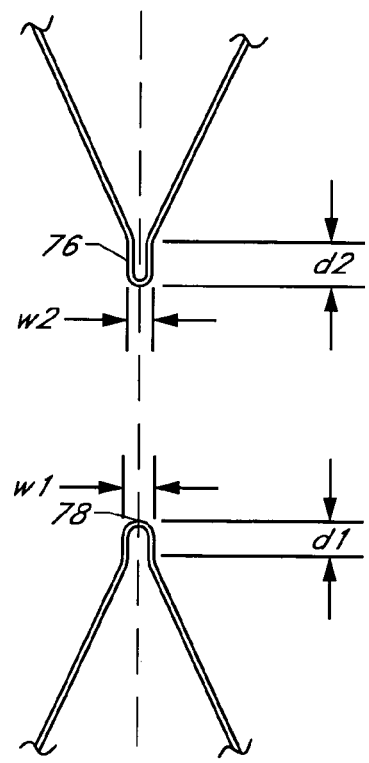
FIG. 6 is an exploded view of two opposing apexes dimensioned for one embodiment of the folded link connection of the present invention.

Referring to FIGS. 5 and 6, one or more apexes 76 is provided with an elongated axial length d2, which permits the apex 76 to be wrapped around a corresponding portion 78 such as an apex of the adjacent segment to provide an interlocking link 70 between two axially adjacent cage segments. In one embodiment of the link 70 produced by the opposing apexes 76 and 78 of FIG. 6, utilizing wire having a diameter from 0.012" to 0.018", d1 is generally within the range of from about 1 mm to about 4 mm and d2 is within the range of from about 5 mm to about 9 mm. In general, a longer d2 dimension permits accommodation for greater axial travel of apex 78 with respect to 76, as will be discussed, thereby permitting greater lateral flexibility of the graft. W1 is within the range of from about 3 mm to about 5 mm, and W2 is sufficiently less than W1 that the apex 76 can fit within the apex 78. Any of a wide variety of specific apex configurations and dimensions can be utilized, as will be apparent to those of skill in the art in view of the disclosure herein. Regardless of the specific dimensions, the end of the apex 76 is advanced through the apex 78, and folded back upon its self to hook the apex 78 therein to provide a link 70 in accordance with the present invention.

Figure 10:
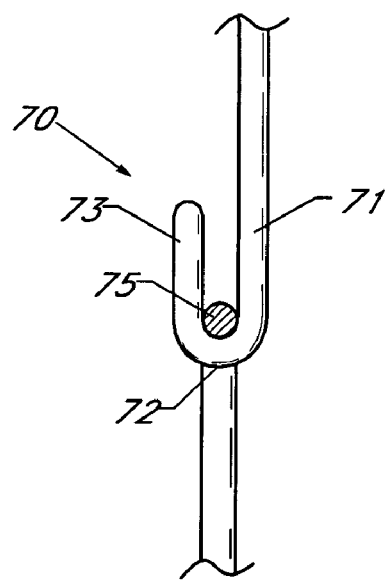
FIG. 10 is a cross-section taken along the line 10-10 in FIG. 9.
Figure 11:
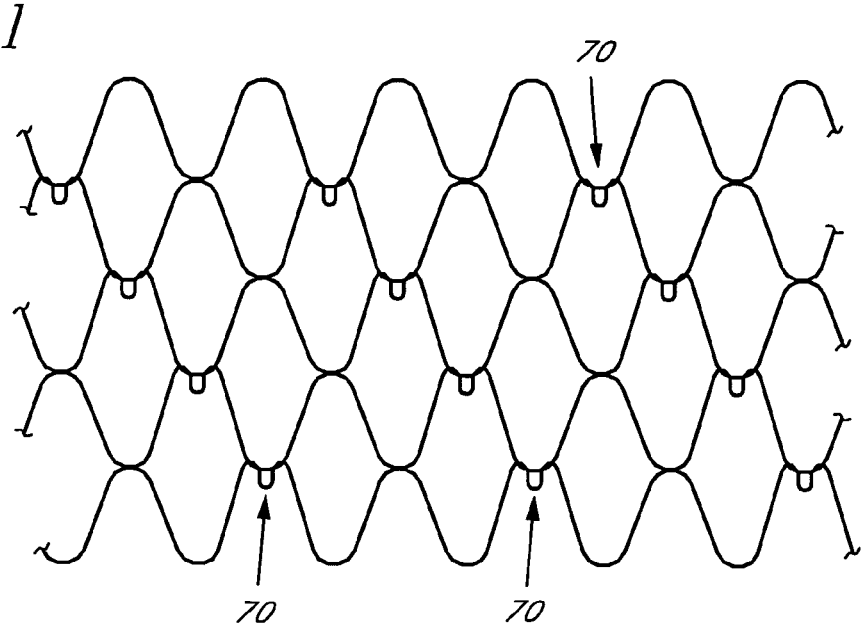
FIG. 11 is a schematic view of a portion of a wall of a graft, laid out flat, illustrating an alternating folded link pattern.

The resulting link 70 (see FIGS. 7 and 8) comprises a wall portion 71 extending in a first direction, substantially parallel to the axis of the graft, and a transverse portion 72 extending transverse to the axis of the graft. A return portion 73 extends generally in the opposite direction from the wall portion 71 to create a generally "U" shaped hook. In certain embodiments, a closing portion 74 is also provided, to minimize the risk of excessive axial compression of the wire cage. The forgoing structure produces a functionally closed aperture 77 (illustrated in FIGS. 8A and 8B), which receives the interlocking section 75 of the adjacent graft segment. Alternatively, see FIG. 10.

In general, the aperture 77 preferably has a width (as viewed in FIG. 8) in the radial graft direction of substantially equal to the radial direction dimension of the interlocking section 75. In this embodiment, the interlocking section 75, as well as the locking portion 71 and return portion 73 can be flattened in the radial direction, to minimize the transverse cross-section of the link 70. In the axial direction, the aperture 77 is preferably greater than the axial direction dimension of the interlocking section 75, to accommodate some axial movement of each adjoining tubular segment of the graft. The axial length of the aperture 77 is at least about 2 times, and preferably at least about 3 or 4 times the cross-section of the interlocking section 75. The optimum axial length of the aperture 77 can be determined through routine experimentation by one of skill in the art in view of the intended clinical performance, taking into account the number of links 70 per transverse plane as well as the desired curvature of the finished graft.

Figure 6A:
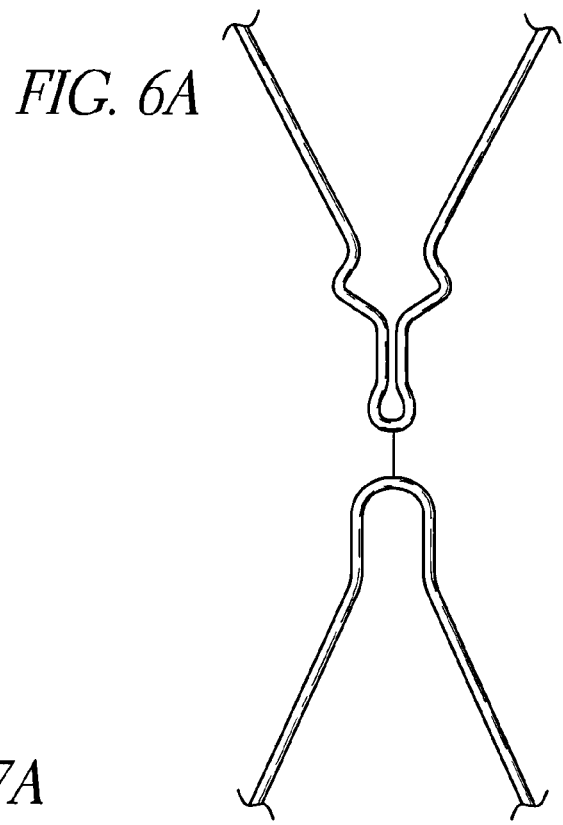
FIGS. 6A, 7A, 8A, 7B, 8B, 7C, and 7D illustrate alternate embodiments of a folded link constructed from an opposing apex pair.
Figure 7A:
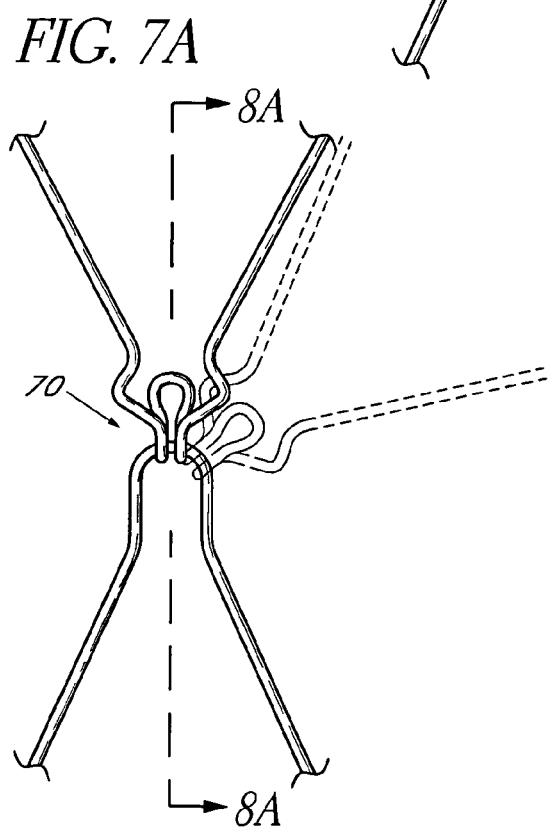
Figure 8A:
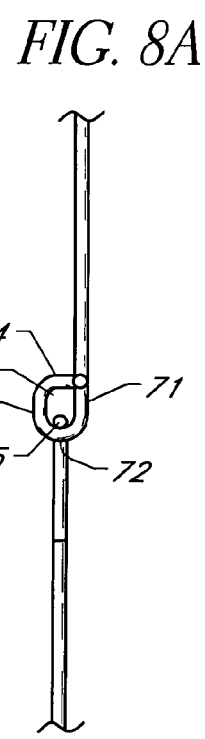
Figure 7:
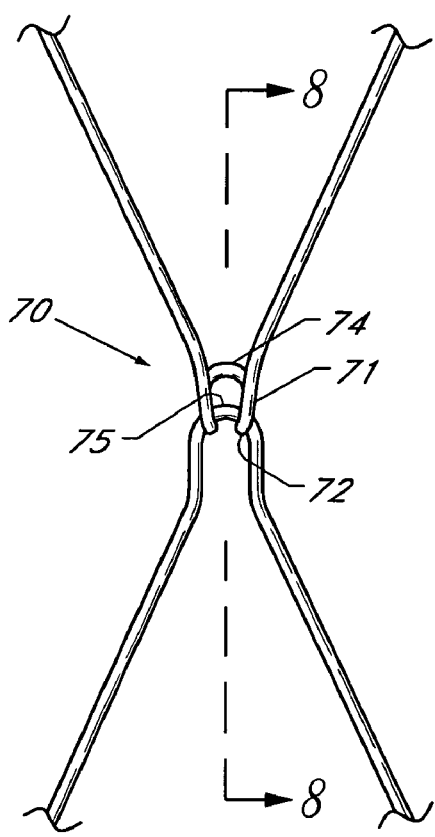
FIG. 7 is an enlarged view of a folded link, taken along the lines 7-7 in FIG. 5.
Figure 8:
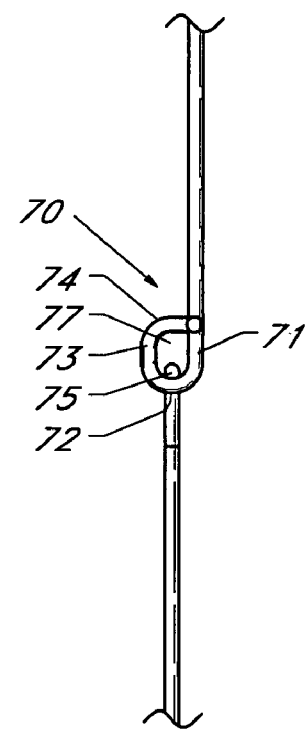
FIG. 8 is a cross-sectional view taken along the line 8-8 in FIG. 7.

FIGS. 6A, 7A and 8A illustrate an alternate configuration for the moveable link 70. With this configuration, the radial expansion force will be higher.

Figure 7B:
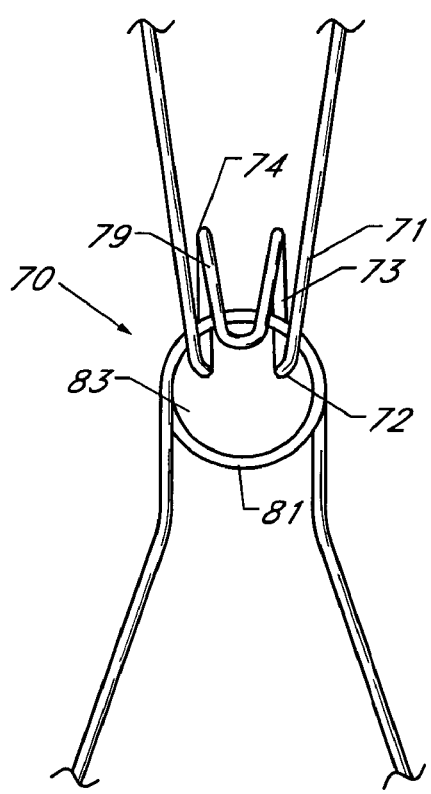
Figure 8B:
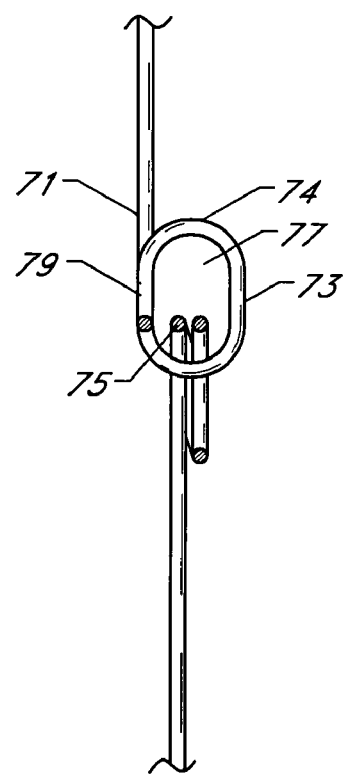

FIGS. 7B and 8B illustrate another alternate configuration. This linkage has a better resistance to axial compression and disengagement. Referring to FIGS. 7B and 8B, the apex extends beyond closing portion 74 and into an axial portion 79 which extends generally parallel to the longitudinal axis of the graft. Provision of an axial extension 79 provides a more secure enclosure for the aperture 77 as will be apparent to those of skill in the art. The embodiments of FIGS. 7B and 8B also illustrate an enclosed aperture 83 on the opposing apex.

Figure 7C:
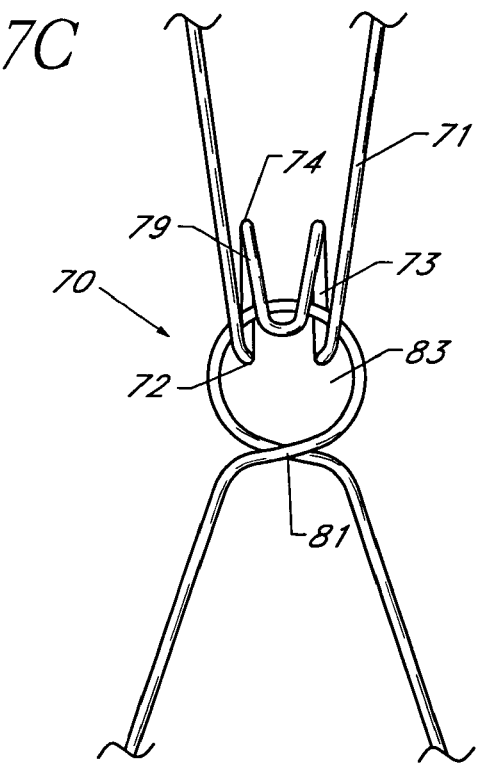
Figure 7D:
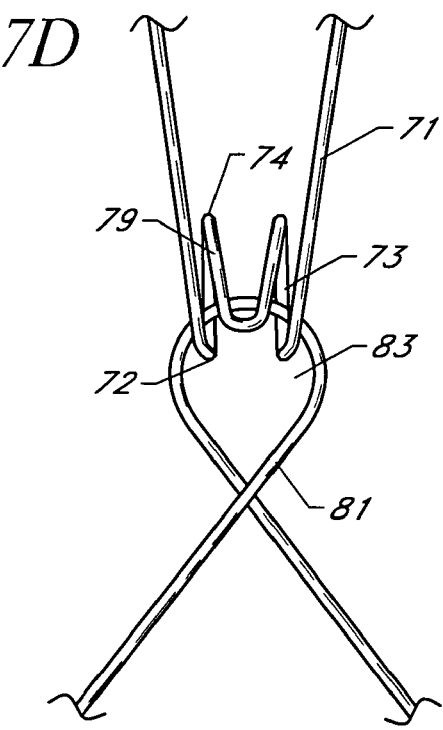

The aperture 83 is formed by wrapping the apex in at least one complete revolution so that a generally circumferentially extending portion 81 is provided. Circumferential portion 81 provides a stop, to limit axial compressibility of the graft. The enclosed aperture 83 can be formed by winding the wire of the apex about a mandrel either in the direction illustrated in FIG. 7B, or the direction illustrated in FIG. 7C. The embodiment of FIG. 7C advantageously provided only a single wire thickness through the aperture 77, thereby minimizing the wall thickness of the graft. This is accomplished by moving the crossover point outside of the aperture 77, as will be apparent from FIG. 7C.

The link 70 in accordance with one embodiment of the present invention is formed integrally with the wire that forms the cage of the endovascular prosthesis. Alternatively, link 70 may be constructed from a separate material that is secured to the wire cage such as by soldering, suture, wrapping or the like.

Figure 9:
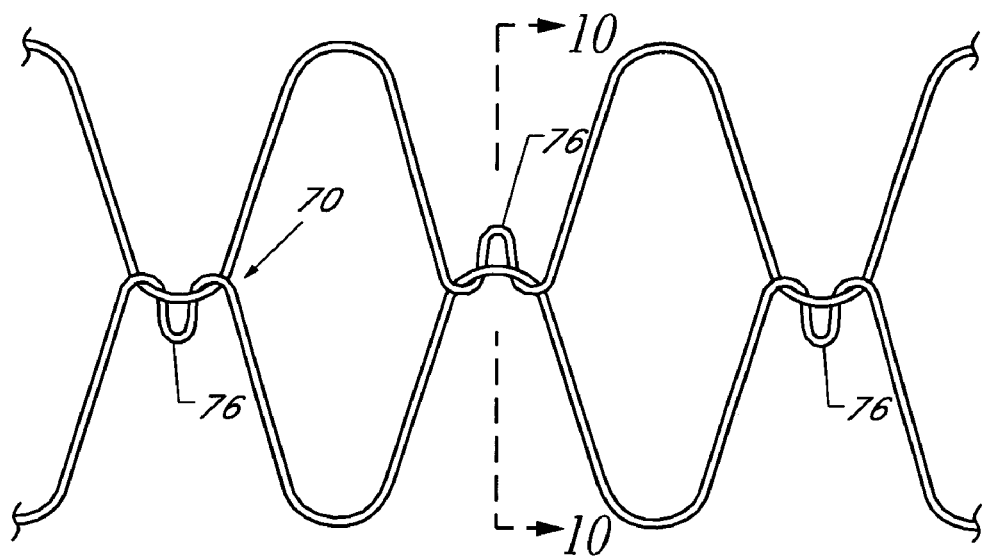
FIG. 9 is a partial view of a junction between two adjacent tubular segments, illustrating oppositely oriented folded links in accordance with the present invention.

The axial direction of the link 70 may also be varied, depending upon the desired performance characteristics of the graft. For example, the distal tips 76 of each link 70 may all face the same direction, such as proximal or distal with respect to the graft. See, for example, FIG. 5. Alternatively, one or more links in a given transverse plane of apexes may face in a proximal direction, and one or more links in the same transverse plane may face in the opposite direction. See, for example, FIG. 9.

Regardless of the axial orientation of the link 70, at least one and preferably at least two links 70 are provided per transverse plane separating adjacent graft segments. In an embodiment having six apexes per transverse plane, preferably at least two or three and in one embodiment all six opposing apex pairs are provided with a link 70. See FIG. 5.

The distribution of the interlocking link 70 throughout the wire cage can thus vary widely, depending upon the desired performance characteristics. For example, each opposing apex pair between adjacent tubular segments can be provided with a link 70. See FIG. 5. Alternatively, interlocking links 70 may be spaced circumferentially apart around the graft wall such as by positioning them at every second or third opposing apex pair.

Figure 12:
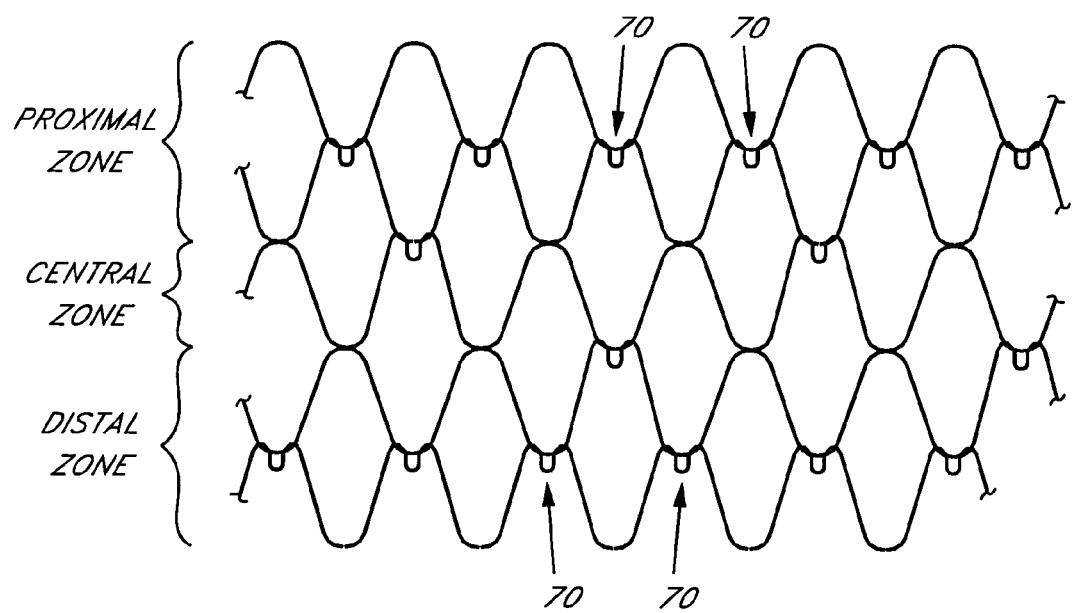
FIG. 12 is a wall pattern as in FIG. 11, illustrating a multi-zone folded link pattern.

The distribution of the links 70 may also be varied along the axial length of the graft. For example, a first zone at a proximal end of the graft and a second zone at a distal end of the graft may be provided with a relatively larger number of links 70 than a third zone in the central portion of the graft. In one embodiment, the transverse apex plane between the first and second tubular segments at the proximal end of the graft may be provided with a link 70 at each opposing apex pair. This has been determined by the present inventors to increase the radial strength of the graft, which may be desirable at the proximal (superior) end of the graft and possibly also at the distal end of the graft where resistance to leakage is an issue. A relatively lesser radial strength may be necessary in the central portion of the graft, where maintaining patency of the lumen is the primary concern. For this reason, relatively fewer links 70 may be utilized in a central zone, in an effort to simplify graft design as well as reduce collapse profile of the graft. See FIG. 12.

In one straight segment graft, having four graft segments, three transverse apex planes are provided. In the proximal apex plane, each opposing pair of apexes is provided with a link 70. In the central transverse apex plane, three of the six apex pairs are provided with a links 70, spaced apart at approximately 120°. Substantially equal circumferential spacing of the link 70 is preferred, to provide relatively uniform resistance to bending regardless of graft position. The distal transverse apex plane may also be provided with a link 70 at each opposing apex pair.

The foregoing interlocking link 70 in accordance with one embodiment of the present invention can be readily adapted to both the straight segment grafts as discussed above, as well as to the bifurcated grafts discussed below.

The interlocking link 70 can be utilized to connect any of a number of independent graft segments in axial alignment to produce either a straight segment or a bifurcation graft. The interlocking link 70 may be utilized as the sole component to secure adjacent segments to each other, or may be supplemented by additional attachment structures such as metal loops, sutures, welds and others which are well understood in the art.

Figure 12A:
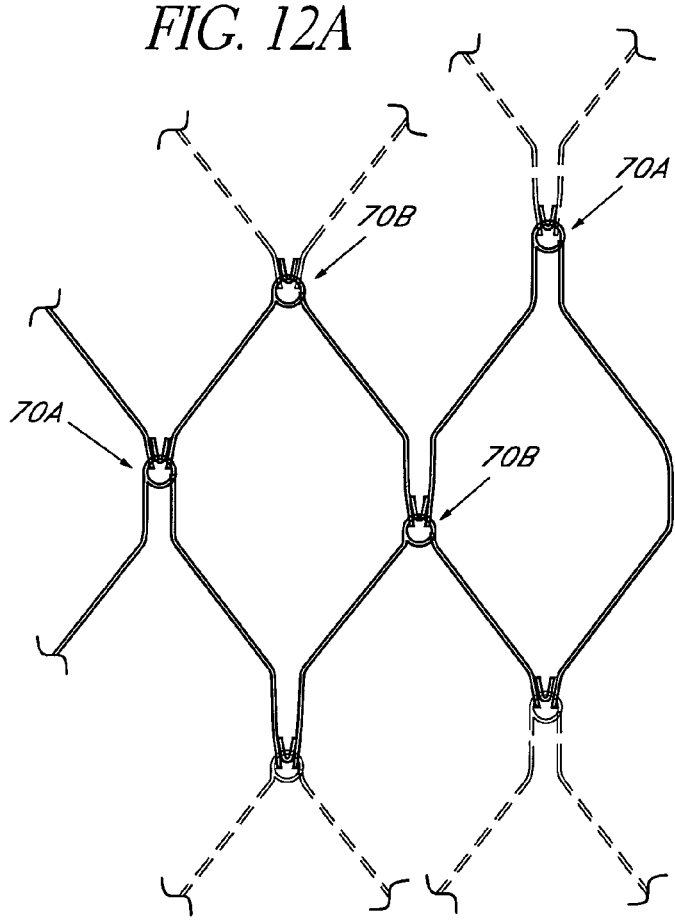
FIGS. 12A through 12C illustrate an alternate wall pattern, which permits axially staggered links between adjacent graft segments.
Figure 12B:
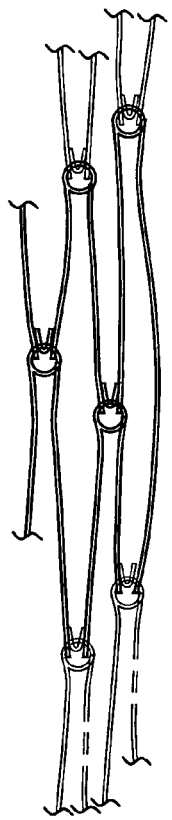
Figure 12C:
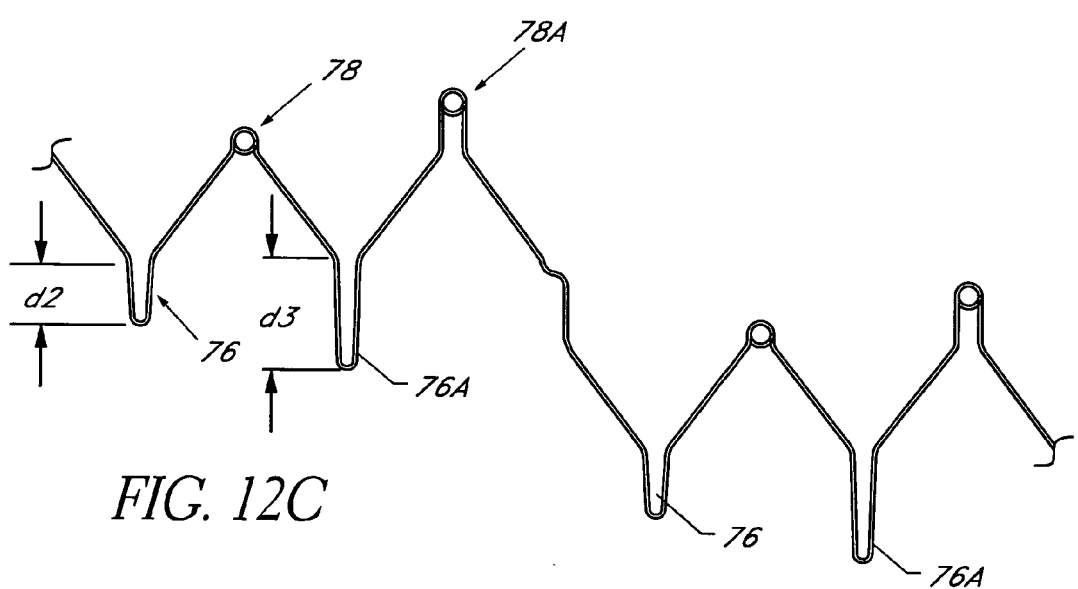

Referring to FIGS. 12A through 12C there is illustrated a further wire layout which allows a smaller collapsed profile for the vascular graft. In general, the embodiment of FIGS. 12A through 12C permits a series of links 70A and 70B to be staggered axially from one another as seen in FIGS. 12A and 12B. In this manner, adjacent links 70 do not lie in the same transverse plane, and permit a tighter nesting of the collapsed wire cage. Preferably, between each adjoining graft segment, at least a first group of links 70A is offset axially from a second group of links 70B. In a six apex graft, having a link 70 at each apex, for example, a first group of every other apex 70A may be positioned slightly proximally of a second group of every other apex 70B. Referring to FIG. 12C, this may be accomplished by extending an apex 76A by a distance d3 which is at least about 1.2 times and as large as 1.5 times or 2 times or more the distance d2. The corresponding apexes 78 and 78A are similarly staggered axially, to produce the staggered interface between adjacent graft segments illustrated in FIG. 12A. Although a loop apex is illustrated in FIG. 12C as apex 78, any of the alternate apexes illustrated herein can be utilized in the staggered apex embodiment of the invention. The zig-zag pattern produced by axially offset links 70A and 70B can reside in a pair of parallel transverse planes extending generally between adjacent segments of the graft. Alternatively, the zig-zag relationship between adjacent links 70A and 70B can spiral around the circumference of a graft in a helical pattern, as will be understood by those of skill in the art in view of the disclosure herein. The precise axial offset between adjacent staggered links 70A and 70B can be optimized by one of ordinary skill in the art through routine experimentation, taking into account the desired physical properties and collapsed profile of the graft.

Additional details and embodiments of the wire layout for the vascular graft described above can be found in U.S. Pat. No. 6,077,296, which is hereby incorporated by reference herein in its entirety.

An alternative, low profile linkage between adjacent segments may be provided by the polymeric sleeve or membrane. In this embodiment, any of the variations of the wire cage illustrated and described with respect to FIGS. 3-12C, may be coated on the inside, the outside, or preferably, on both the inside and the outside, by a polymeric sleeve, preferably of a laminated structure, which creates a flexible polymeric linkage of very low profile. In one embodiment, where the wire cage is embedded between inner and outer layer(s) of polymeric material, the inner layer(s) may be adhered to the outer layer(s) through the openings between the adjacent wires of the support. The various mechanical linkages between adjacent segments of previously disclosed embodiments may be reduced in number or omitted when the embedding technology described below is used. Instead the ePTFE layer retains the desired spatial relationship between adjacent graft segments.

The sleeve or membrane that is used to cover the tubular wire graft cage can be manufactured from any of a variety of synthetic polymeric materials, or combinations thereof, including DACRON®, polyester, polyethylene, polypropylene, fluoropolymers, polyurethane foamed films, silicon, nylon, silk, thin sheets of super-elastic materials, woven materials, polyethylene terephthalate (PET), or any other biocompatible material. In one embodiment of the present invention, the membrane material is a fluoropolymer, in particular, expanded polytetrafluoroethylene (ePTFE) having a node-fibril structure. The ePTFE membrane used in the present invention is manufactured from thin films of ePTFE that are each approximately 0.0025 to 0.025 mm in thickness. Thus, the films could be 0.0025, 0.0050, 0.0075, 0.0100, 0.0125, 0.0150, 0.0175, 0.0200, 0.0225, and 0.0250 mm thick.

From 1 to about 200 plies (layers) of ePTFE film may be stacked up and laminated to one another to obtain a membrane with the desired mechanical and structural properties. The ePTFE composite or stack may, if desired, exhibit the neointima inhibiting properties described elsewhere herein. An even number of layers are preferably stacked together (e.g., 2, 4, 6, 8, 10, etc.), with approximately 2 to 20 layers being desirable. Cross-lamination occurs by placing superimposed sheets on one another such that the film drawing direction, or stretching direction, of each sheet is angularly offset by angles between 0 degrees and 180 degrees from adjacent layers or plies. Because the base ePTFE is thin, as thin as 0.0025 mm thick, superimposed films can be rotated relative to one another to improve mechanical properties of the membrane. In one preferred embodiment, the membrane is manufactured by laminating between 4 to 8 plies of ePTFE film, each film ply being about 0.0125 mm thick.

In this embodiment, the membrane is made by laminating 4 plies of ePTFE film, each film being about 0.0125 mm thick. The laminated ePTFE sheets are then sintered together at temperatures of about 370° C., under vacuum to adhere the film layers to one another. The resultant 8-ply laminate structure is typically 0.0375 mm thick. Additional details and variations on the ePTFE laminating technology are disclosed in U.S. Pat. No. 5,925,075 to Myers et al. the disclosure of which is herein incorporated in its entirety by reference thereto.

Figure 13A:
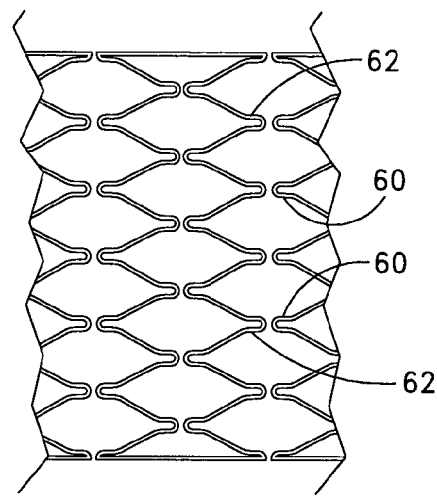
FIGS. 13A through 13D show alternative zig-zag wire or laser cut sheet support configurations that vary from the support illustrated in FIG. 3.

Any of the variations of formed wire configurations disclosed herein, particularly those described with reference to FIGS. 13A-E, may be coated on the lumenal (inner) and/or external surface, or embedded within a laminated ePTFE membrane in accordance with the present invention. For example, as shown in FIG. 13A, separate zig-zag segments, similar to those illustrated in FIG. 3, but lacking the connector 66, may be positioned at a substantially fixed axial distance from one another by embedding in an ePTFE membrane. In the FIG. 13A variation, the adjacent segments are rotationally positioned with respect to each other so that the proximal bends 60 from one segment align with the distal bends 62 from the adjacent segment. Thus, the axial length of a graft or graft portion formed by two adjacent segments is greater than or equal to the sum of the axial length of each individual segment.

The axial compressability, radial strength, and lateral flexibility of a graft utilizing the structure illustrated in FIG. 13A will be influenced by the various factors discussed previously herein, as well as by the spacing in an axial direction between adjacent proximal bends 60 and corresponding distal bends 62 on the adjacent segment. For example, as the axial spacing is increased, greater lateral flexibility may be achieved. However, axial compression of the graft may occur at a lower compressive force level, depending upon the structural integrity of the embedded PTFE wall. Specific axial spacings may be optimized for particular applications, depending upon the desired performance. In general, an axial separation between each proximal bend 60 and corresponding distal bend 62 will be within the range of from about 0 to about 3 mm. Preferably, the spacing in a straight segment graft utilizing a wire diameter of about 0.014" will be within the range of from about 0.5 mm to about 1.5 mm.

Figure 13B:
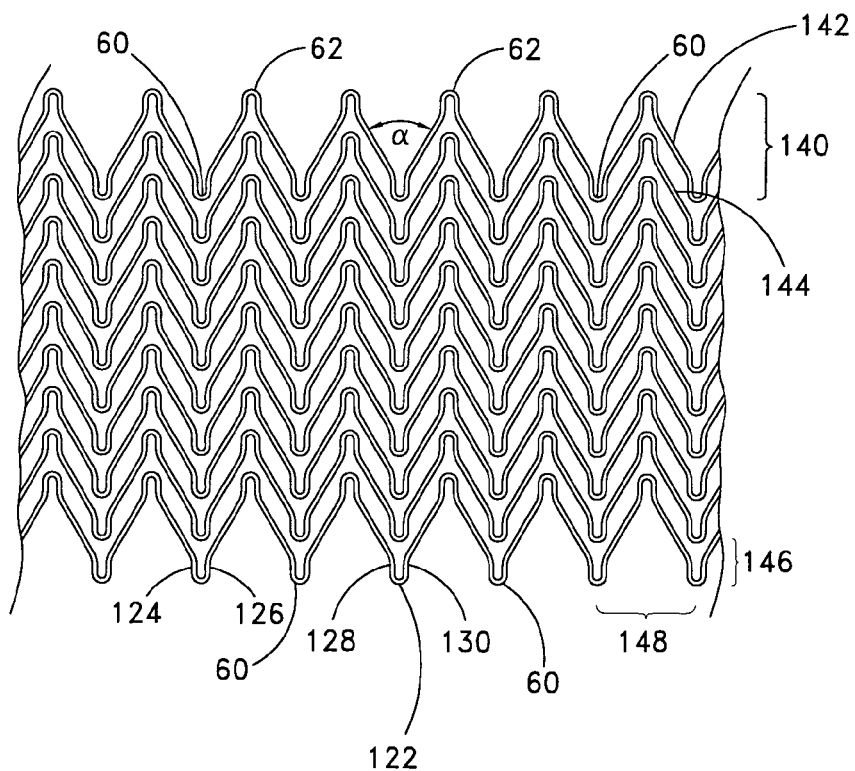

In another variation, shown in FIG. 13B, the separate zig-zag segments are rotationally aligned. In the illustrated configuration, adjacent segments 54 are nested within adjacent segments, such that each proximal bend 60 from a distal segment lies within angle α between two distal bends 62 of a proximal segment. In this embodiment, the axial length formed by two adjacent segments is less than the sum of the axial length 140 of each individual segment. This design may be beneficial in applications where greater radial support is desired.

Alternatively, a first segment 142 may be spaced axially apart from a second segment 144, such that the axial distance between a distal bend 62 on first segment 142 and distal bend 62 on second segment 144 exceeds the axial length 140 of the segment. Axial distances between two adjoining segments 142 and 144 may vary within the range of from about 100% to about 200% of the length 140 of the adjacent segment 142, depending upon the desired radial force and column strength of the resulting graft.

In the embodiment illustrated in FIG. 13B, ten segments are illustrated in a nested configuration, in which no interconnecting links are used to secure adjacent segments 54 to each other. Thus, the spatial relationship between adjacent segments 54 is maintained by the fabric or polymer layer or layers, to which the segments 54 are adhered and/or embedded.

In one nested embodiment having a 0.014" filament and the wall pattern illustrated in FIG. 13B, the circumferential distance 148 between any pair of adjacent distal bends 62 or proximal bends 60 is about 0.82Δ. The axial distance 146 between a proximal bend 60 and adjacent distal bends 62 is approximately 0.77". The axial length of the first leg 124 and second leg 126 between apex 122 and first bend 128 or second bend 130 is approximately 0.10". See FIG. 13E.

Figure 13C:
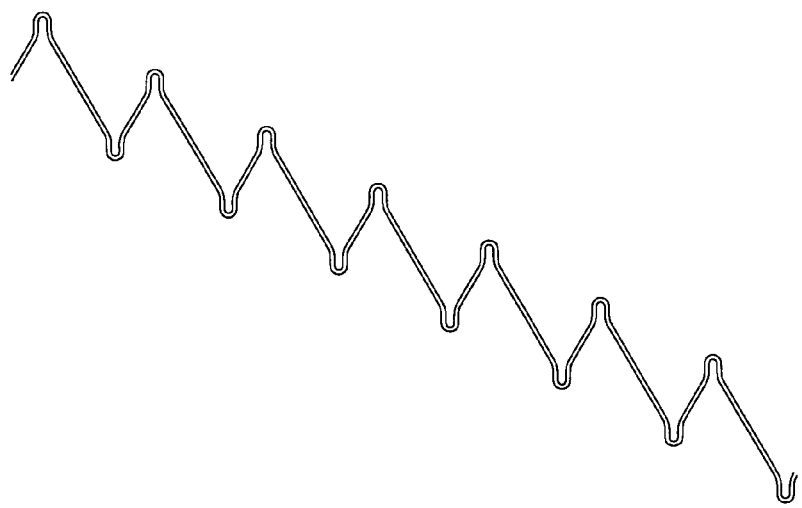

An alternative design is illustrated in FIG. 13C. In this variation of the wire support, a single length of wire or laser cut filament from sheet stock is formed into a zig-zag pattern which is adapted to be rolled to form a spiral configuration, such as disclosed by An et al., U.S. Pat. No. 5,545,211, which is herein incorporated in its entirety by reference thereto. Unlike An, however, axially adjacent apexes in the wire support do not need to be interlinked. Thus, the present embodiment may be constructed without interlinking axially adjacent apexes as disclosed, for example, in U.S. Pat. No. 5,217,483 to Tower, the disclosure of which is incorporated in its entirety herein by reference. The resulting wire cage design is thus similar to that disclosed in U.S. Pat. No. 5,665,115 to Cragg, the disclosure of which is incorporated in its entirety herein by reference, after deletion of the loop members 12. Deletion of loop members 12 from the Cragg design is enabled by embedding the wire cage of the present invention in the multi-layer ePTFE or other polymeric membrane as disclosed herein.

Although previous embodiments have been described primarily in the context of formed wire, the embodiments of FIGS. 13A-E may conveniently be formed from a flat sheet or tube of material such as Elgiloy, Nitinol, or other material having desired physical properties. Sheets having a thickness of no more than about 0.025" and, preferably, no more than about 0.015" are useful for this purpose. In one embodiment, the support structure is formed by laser cutting the appropriate pattern on a 0.014" thickness Elgiloy foil or tube. Similarly, any of the other embodiments disclosed previously herein can be manufactured by laser cutting, chemical etching, or otherwise forming the wire cage support from a flat sheet or tube of Elgiloy or other suitable material.

Figure 13D:
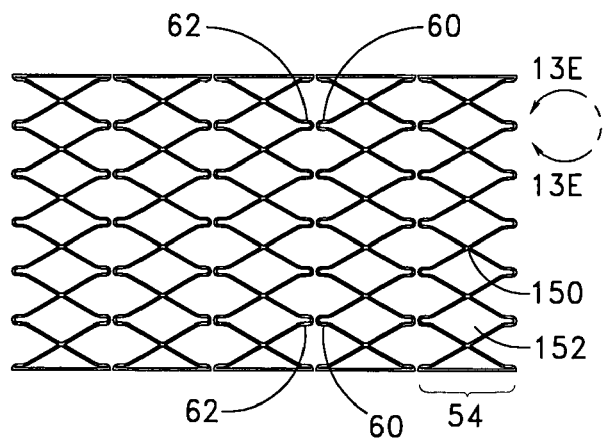

One advantage of forming the wire cage such as by laser cutting is the ability to more precisely control the cross-sectional area of the filament at different points in the structure. For example, filament crossover points can be readily manufactured having only a single filament thickness, compared to a double filament thickness where the crossover is accomplished in a wire structure. Referring to FIG. 13D, there is illustrated a side wall pattern for a self-expandable vascular graft in which each segment 54 comprises a plurality of diamond-shaped cells 152 each having a proximal bend 60 and a distal bend 62. At junction 150, the radial wall thickness of the support structure would be two filament thicknesses if this structure were constructed from preformed wire. However, by cutting the structure of FIG. 13D from a solid walled tube or thin film sheet, the junction 150 may have the same thickness as any other portion of the filament, thereby minimizing the profile of the resulting graft. Adjacent segments 54 may be held with respect to each other by a polymeric layer such as PTFE, as is described elsewhere herein.

Figure 13E:
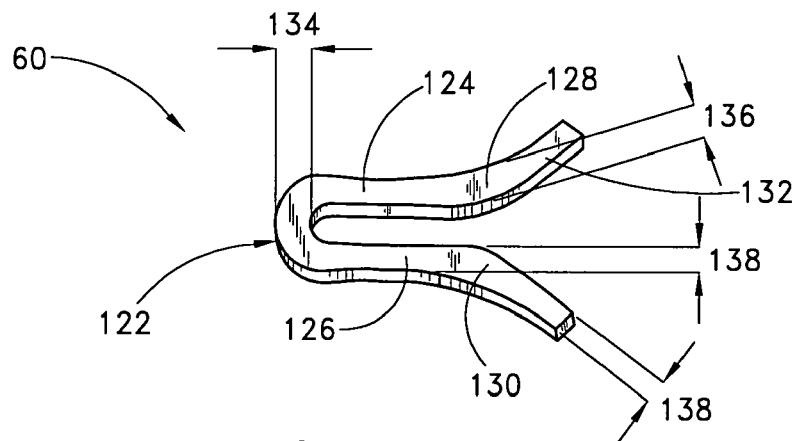
FIG. 13E is a detail view of a bend identified in FIG. 13D, illustrating a varied filament width feature of the invention
Figure 13F:
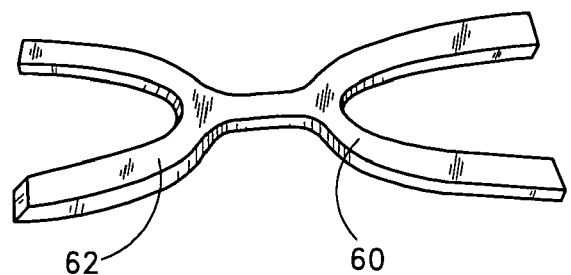
FIG. 13F is a detail view of an integral link between opposing apexes.

Another example of design flexibility, which can be achieved using the laser cutting technique of another embodiment of the present invention, is illustrated in FIG. 13E. Referring to FIG. 13E, a detailed view is illustrated of either a proximal bend 60 or distal bend 62 (as shown in FIG. 13F). In any embodiment having only a few or no interconnecting links between adjacent segments 54, the radial strength in the finished product will tend to be lower than the radial strength of a product with multiple interconnecting links between adjacent segments 54 in an otherwise comparable graft. As an alternate or supplement to adding interconnecting links between adjacent segments 54, the cross-sectional area of the filament 132 may be varied to affect the radial strength.

For example, the plan view of the filament 132 in the area of a bend 60 as seen in FIG. 13E has a first width in the relatively straight sections thereof, and a second, greater width in the bends, and a constant thickness throughout. In one embodiment, the bend 60 comprises an apex 122 in which the filament 132 has a width 134 of about 0.020". Each of a first leg 124 and second leg 126 has a width at least one point of about 0.014". Thus, in the first and second leg sections, the transverse cross-section of the filament 132 is approximately square since, in this embodiment, it has been cut from a sheet having a thickness of 0.014". A first bend 128 and a second bend 130 each have a maximum width of approximately 0.020". The width in a bend is preferably at least about 110% and more preferably at least about 125% of the average width in the adjacent filament. Bend widths of greater than about 140% or 150% of the adjacent filament width may also be used. The foregoing values can be readily converted to cross sectional areas to apply the same concept where the filament enlargement in the area of a bend occurs in whole or in part in the radial instead of the circumferential direction.

By enlarging the cross-sectional area of the filament 132 in the area of apex 122, first bend 128 and second bend 130, particularly in the circumferential direction of the graft, the inventors have determined that the relative radial strength of the device can be increased while omitting or minimizing connecting links between adjacent segments 54. In this embodiment, the apex 122 has an outside radius of curvature of about 0.027", and an inside radius of curvature of about 0.011". The radius of curvature of the concave surface of the filament 132 in the area of first bend 128 or second bend 130 is approximately 0.15". The radius of the corresponding convex surface of each of the first bend 128 and second bend 130 is approximately 0.05". Any of the foregoing dimensions or radii can be varied considerably, within the scope of the present invention, to achieve particular physical property characteristics, as will be apparent to those of skill in the art.

If the foregoing floating segment embodiments exhibit inadequate column strength or radial strength, one or more links may be utilized to connect each adjacent pair of segments such as 142 and 144. Depending upon the degree of increased radial or column strength desired in the finished product, two or three or four or more links may be provided between each pair of segments 54. In one embodiment, at least one and as many as two or three or more links may be utilized for each adjacent pair of segments.

In addition, where links are desired between adjacent segments 54, links cut from a metal or other material tube or sheet can also be integrally formed with the adjacent segments 54 without adding wall thickness to the wire cage. See FIG. 13F.

Figure 14:
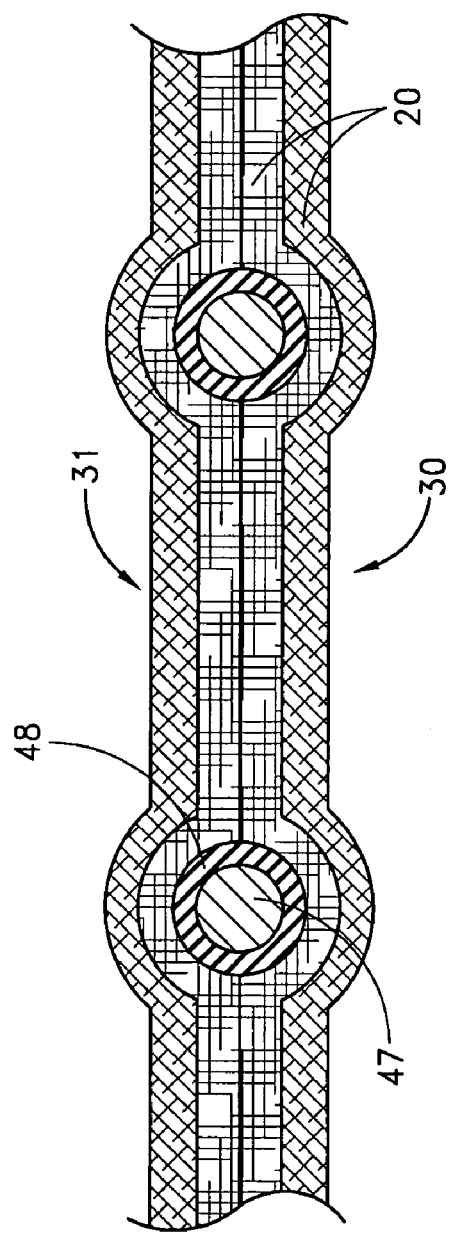
FIG. 14 is a cross-sectional view taken through a portion of a prosthesis in which a wire support is embedded in an ePTFE wall.

Regardless of the particular configuration of wire cage, a cross section of an the embedded support can be appreciated with reference to FIG. 14. The wire 47 has a thin coating 48, which comprises a thermoplastic polymer adhesive, such as for example, FEP. In one embodiment, the coated wire is embedded within at least two layers of polymer film 20, such as for example, ePTFE, one each on the lumenal (inner) surface 30 and exterior surface 31. The embedded support depicted in FIG. 14 is shown having two plies on each of the lumenal and external surfaces. As detailed above, however, preferably an even number of layers are stacked together (e.g., 2, 4, 6, 8, 10, etc.), with approximately 2 to 20 layers being desirable. Cross-lamination of superimposed sheets, each sheet angularly offset by angles between about 0 degrees and about 180 degrees from adjacent sheet layers, may be desired in order to improve mechanical properties of the membrane. As discussed in more detail above, the membrane may be manufactured by laminating between 4 to 8 plies of ePTFE film, each film ply being about 0.0125 mm thick. The laminated ePTFE sheets, fused together at temperatures of about 370° C. under vacuum, form a low profile, flexible linkage between adjacent segments of the wire cage.

Other graft configurations and methods of coating wire stents with uniaxially and/or biaxially oriented ePTFE are encompassed by the present invention. One such alternate method is disclosed in U.S. Pat. No. 5,788,626 to Thompson, which is herein incorporated in its entirety by reference thereto.

Another embodiment of the present invention may be appreciated with reference to FIGS. 15A-C. In FIG. 15A, a two segment portion of the wire cage is shown in which the proximal 60 and distal 62 apexes from adjacent segments of the tubular member are aligned in the longitudinal axis, thereby essentially abutting one another as illustrated. In this variation, the wire cage is surrounded by a polymeric sleeve 44, preferably at least two ePTFE membranes, one along the lumenal surface and one along the exterior surface of the stent. The membranes may comprises any number of plies as discussed above. Alternatively, both surfaces of the cage may be covered by a single tube of ePTFE membrane (1-200 plys) extending through and folded over the wire cage resulting in a layer of ePTFE along both the lumenal and exterior surfaces. In either case, the PTFE envelope is spot welded in a pattern such as that shown in FIG. 15A, wherein the lumenal and exterior membranes are heat-fused in a plurality of spots 101. By spot-welding along the proximal and distal edges of the tubular member, the sleeve is closed around the support.

Further, the pattern of four welding spots surrounding each apical junction, acts as a flexible linkage, thereby limiting movement of adjacent segments relative to one another. In areas of the graft in between the welding spots, the lumenal and exterior membranes are not necessarily fused.

As shown in end elevation from the distal margin of the graft (along line C-C) in FIG. 15C, the inner 30 and outer 31 membranes are fused at the welding spots 101, whereas the membrane layers can separate in between the welding spots. The sleeve is also illustrated surrounding the wire apexes 62. This design, like the previous variations in which the lumenal and exterior membranes were fused in all areas between adjacent wires, presents a very low profile, since the thickness of the PTFE membranes can be very small, as detailed above.

An alternative configuration is illustrated in FIG. 15B, wherein axially adjacent apexes of the support cage are circumferentially offset, such that distal apexes 62 from the adjacent segments are aligned with one another in the longitudinal axis (and proximal apexes 60 from adjacent segments are aligned with one another in the longitudinal axis). In this embodiment, the distal apex 62 from a proximal segment is oriented between two adjacent proximal apexes 60 of the distal segment. As in FIG. 15A, the tubular wire segments are surrounded on both sides by a polymeric sleeve 44. An identical pattern of welding spots 101 is used to fasten the inner and outer membranes at the axial ends of the tubular member. Thus, the thin end elevation wall profile (shown in FIG. 15C) for the graft variation shown in FIG. 15B would be the same as that presented by the graft of FIG. 15A. However, along the length of the graft, at the junctions between adjacent tubular wire segments, the pattern of welding spots is different than that shown in FIG. 15B. In the inside angle of each apex, the membranes are spot welded. Further, in a preferred variation, at least alternating distal and proximal apexes and preferably all apexes may be surrounded by several spot welds. The precise pattern is not critical as long as the spot welds serve the purpose of securing the inner and outer polymer layers together and minimizing movement between adjacent segments in the longitudinal (or axial) direction.

The spot welding of the two membrane layers may be accomplished by any spot heating method or apparatus known in the art. For example, a pointed heating iron, like a conventional soldering iron, could be used as long as it was adapted to maintain a membrane temperature sufficient to bond the layers of polymer film together. Typically for ePTFE, a temperature of 370° for about 15 minutes would be sufficient to fuse the layers together. In one preferred method of spot welding the lumenal and exterior PTFE membranes, an RF chamber may be programmed to make all of the necessary welds at once.

In one embodiment of the invention, the material of the ePTFE membrane or sleeve is sufficiently porous to permit ingrowth of endothelial cells into, but not through the sleeve wall. Such controlled ingrowth may provide more secure anchorage of the prosthesis and potentially reducing flow resistance, sheer forces, and leakage of blood around the prosthesis.

The polymeric sleeve may be configured to prevent leakage of fluid through the sleeve wall and into an aortic aneurysm sack. The sleeve provides a seal across the aneurysm and substantially prevents even micro amounts of leakage flow (i.e., the seeping of fluid through the porous architecture of the sleeve membrane) through the sleeve wall. Even micro amounts of leakage flow can increase the pressure in the aneurysm sack, and over time may cause the sack to grow and possibly rupture. Accordingly, in one embodiment, the sleeve prevents fluids, including blood components such as serum, from penetrating, leaking, or seeping through the sleeve wall at standard anatomical pressures.

The ability of a sleeve to prevent micro leaks may be assessed in vitro by pressurizing the sleeve from its luminal surface with water, and observing the formation of water droplets on the sleeve's abluminal or outer, low pressure surface. The pressure at which water will form droplets visible to the unaided eye on the low pressure side of the membrane is known as the water entry pressure. In general, sleeves in accordance with the present invention have a water entry pressure of at least about 3 psi, and in another embodiment, the water entry pressure is at least about 5 psi or about 8 psi, and often at least about 10 psi. In some applications the water entry pressure is at least about 15 psi. For certain abdominal aortic aneurysm applications, the polymeric sleeve will have a water entry pressure within the range of from about 10 psi to about 24 psi.

The porosity characteristics of the polymeric sleeve may be either homogeneous throughout the axial length of the prosthesis, or may vary according to the axial position along the prosthesis. For example, referring to FIGS. 1 and 2, different physical properties will be called upon at different axial positions along the prosthesis 42 in use. At least a proximal landing portion 55 and a distal landing portion 59 of the prosthesis 42 will seat against the native vessel wall, proximally and distally of the aneurysm. In these proximal and distal portions, the prosthesis may be configured to encourage endothelial growth, or at least permit endothelial growth to infiltrate portions of the prosthesis in order to enhance anchoring and minimize leakage. A central portion 57 of the prosthesis spans the aneurysm, and anchoring is less of an issue. Instead, maximizing lumen diameter and minimizing blood flow through the prosthesis wall become more important. Thus, in a central zone 57 of the prosthesis 42, the polymeric membrane or sleeve 44 may either be nonporous, or provided with pores of relatively lower porosity A multi-zoned prosthesis 42 may also be provided in accordance with the present invention by positioning a tubular sleeve 44 on a central portion 57 of the prosthesis, such that it spans the aneurysm to be treated, but leaving a proximal attachment zone 55 and a distal attachment zone 59 of the prosthesis 42 having exposed wires from the wire support 46. In this embodiment, the exposed wires 46 are positioned in contact with the vessel wall both proximally and distally of the aneurysm, such that the wire, over time, may become embedded in cell growth on the interior surface of the vessel wall.

Figure 2:
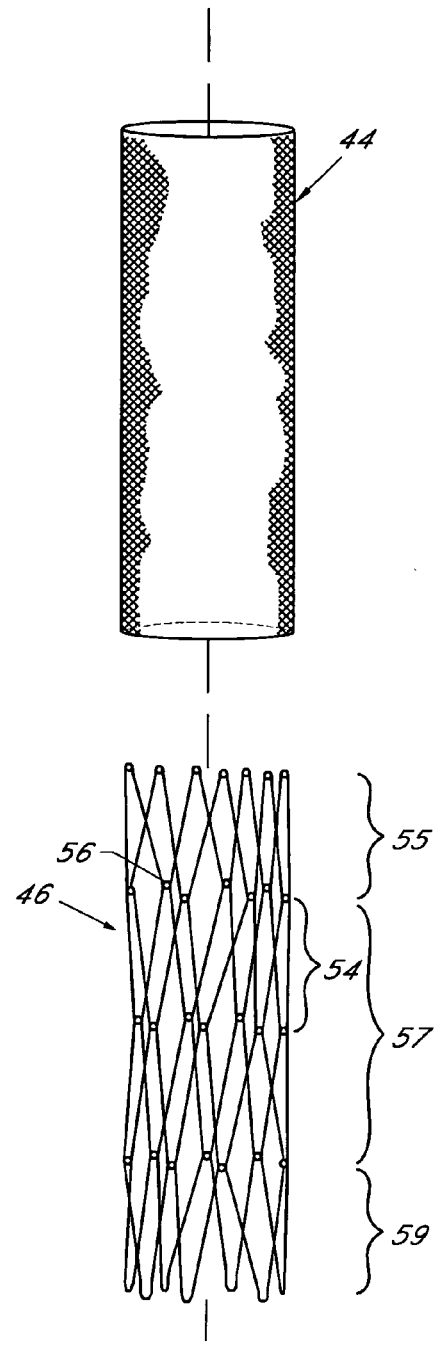
FIG. 2 is an exploded view of an endolumenal vascular prosthesis in accordance with the present invention, showing a self expandable wire support structure separated from an outer tubular sleeve.

In one embodiment of the prosthesis 42, the sleeve 44 and/or the wire support 46 is tapered, having a relatively larger expanded diameter at the proximal end 50 compared to the distal end 52. The tapered design may allow the prosthesis to conform better to the natural decreasing distal cross-section of the vessel, to reduce the risk of graft migration and potentially create better flow dynamics. The cage 46 can be provided with a proximal zone 55 and distal zone 59 that have a larger average expanded diameter than the central zone 57, as illustrated in FIG. 2. This configuration may desirably resist migration of the prosthesis within the vessel and reduce leakage around the ends of the prosthesis.

Referring to FIGS. 16 and 17, a straight segment deployment device and method in accordance with a preferred embodiment of the present invention are illustrated. A delivery catheter 80, having a dilator tip 82, is advanced along guidewire 84 until the (anatomically) proximal end 50 of the collapsed endolumenal vascular prosthesis 88 is positioned between the renal arteries 32 and 34 and the aneurysm 40. The collapsed prosthesis in accordance with the present invention has a diameter in the range of about 2 to about 10 mm. Generally, the diameter of the collapsed prosthesis is in the range of about 3 to 6 mm (12 to 18 French). Preferably, the delivery catheter including the prosthesis will be 16 F, or 15 F or 14 F or smaller.

The prosthesis 88 is maintained in its collapsed configuration by the restraining walls of the tubular delivery catheter 80, such that removal of this restraint would allow the prosthesis to self expand. Radiopaque marker material may be incorporated into the delivery catheter 80, and/or the prosthesis 88, at least at both the proximal and distal ends, to facilitate monitoring of prosthesis position. The dilator tip 82 is bonded to an internal catheter core 92, as illustrated in FIG. 17, so that the internal catheter core 92 and the partially expanded prosthesis 88 are revealed as the outer sheath of the delivery catheter 80 is retracted.

As the outer sheath is retracted, the collapsed prosthesis 88 remains substantially fixed axially relative to the internal catheter core 92 and consequently, self-expands at a predetermined vascular site as illustrated in FIG. 17. Continued retraction of the outer sheath results in complete deployment of the graft. After deployment, the expanded endolumenal vascular prosthesis 88 has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

In addition to, or in place of, the outer sheath described above, the prosthesis 88 may be maintained in its collapsed configuration by a restraining lace, which may be woven through the prosthesis or wrapped around the outside of the prosthesis in the collapsed reduced diameter. Following placement of the prosthesis at the treatment site, the lace can be proximally retracted from the prosthesis thereby releasing it to self expand at the treatment site. The lace may comprise any of a variety of materials, such as sutures, strips of PTFE, FEP, polyester fiber, and others as will be apparent to those of skill in the art in view of the disclosure herein. The restraining lace may extend proximally through a lumen in the delivery catheter or outside of the catheter to a proximal control. The control may be a pull-tab or ring, rotatable reel, slider switch or other structure for permitting proximal retraction of the lace. The lace may extend continuously throughout the length of the catheter, or may be joined to another axially moveable element such as a pull wire.

In general, the expanded diameter of the graft in accordance with the present invention can be any diameter useful for the intended lumen or hollow organ in which the graft is to be deployed. For most arterial vascular applications, the expanded size will be within the range of from about 10 to about 40 mm. Abdominal aortic applications will generally require a graft having an expanded diameter within the range of from about 20 to about 28 mm, and, for example, a graft on the order of about 45 mm may be useful in the thoracic artery. The foregoing dimensions refer to the expanded size of the graft in an unconstrained configuration, such as on the table. In general, the graft will be positioned within an artery having a slightly smaller interior cross-section than the expanded size of the graft. This enables the graft to maintain a slight positive pressure against the wall of the artery, to assist in retention of the graft during the period of time prior to endothelialization of the polymeric sleeve 44.

The radial force exerted by the proximal segment 94 of the prosthesis against the walls of the aorta 30 provides a seal against the leakage of blood around the vascular prosthesis and tends to prevent axial migration of the deployed prosthesis. As discussed above, this radial force can be modified as required through manipulation of various design parameters, including the axial length of the segment and the bend configurations. In another embodiment of the present invention, radial tension can be enhanced at the proximal, upstream end by increasing the wire gauge in the proximal zone. Wire diameter may range from about 0.001 to 0.01 inches in the distal region to a range of from about 0.01 to 0.03 inches in the proximal region.

An alternative embodiment of the wire layout which would cause the radial tension to progressively decrease from the proximal segments to the distal segments, involves a progressive or step-wise decrease in the wire gauge throughout the entire wire support, from about 0.01 to 0.03 inches at the proximal end to about 0.002 to 0.01 inches at the distal end. Such an embodiment, may be used to create a tapered prosthesis. Alternatively, the wire gauge may be thicker at both the proximal and distal ends, in order to insure greater radial tension and thus, sealing capacity. Thus, for instance, the wire gauge in the proximal and distal segments may about 0.01 to 0.03 inches, whereas the intervening segments may be constructed of thinner wire, in the range of about 0.001 to 0.01 inches.

Figure 18:
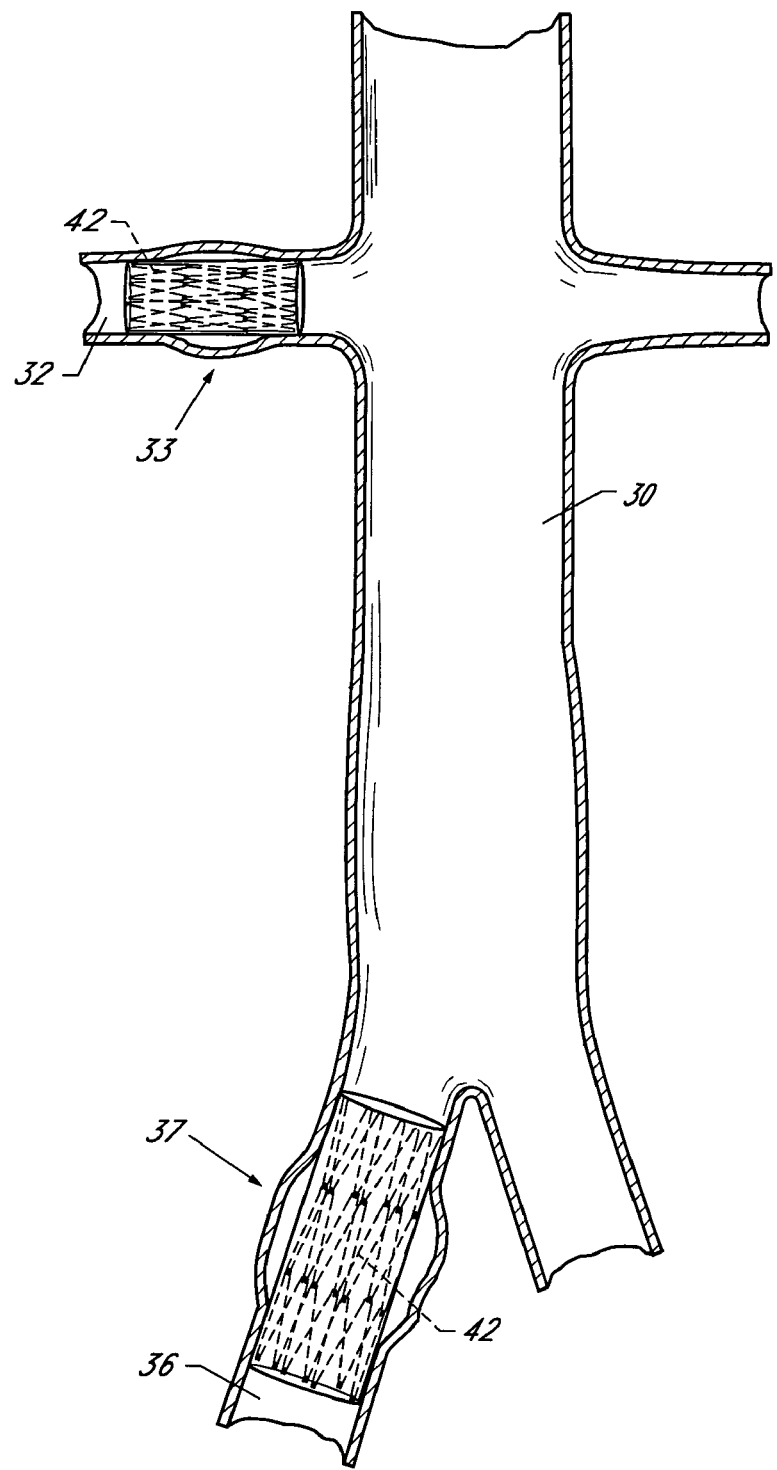
FIG. 18 is a schematic representation of the abdominal aortic anatomy, with an endolumenal vascular prostheses of the present invention positioned within each of the right renal artery and the right common iliac.

Referring to FIG. 18, there is illustrated two alternative deployment sites for the endolumenal vascular prosthesis 42 of the present invention. For example, an aneurysm 33 is illustrated in the right renal artery 32. An expanded endolumenal vascular prosthesis 42, in accordance with the present invention, is illustrated spanning that aneurysm 33. Similarly, an aneurysm 37 of the right common iliac 36 is shown, with a prosthesis 42 deployed to span the iliac aneurysm 37.

Figure 19:
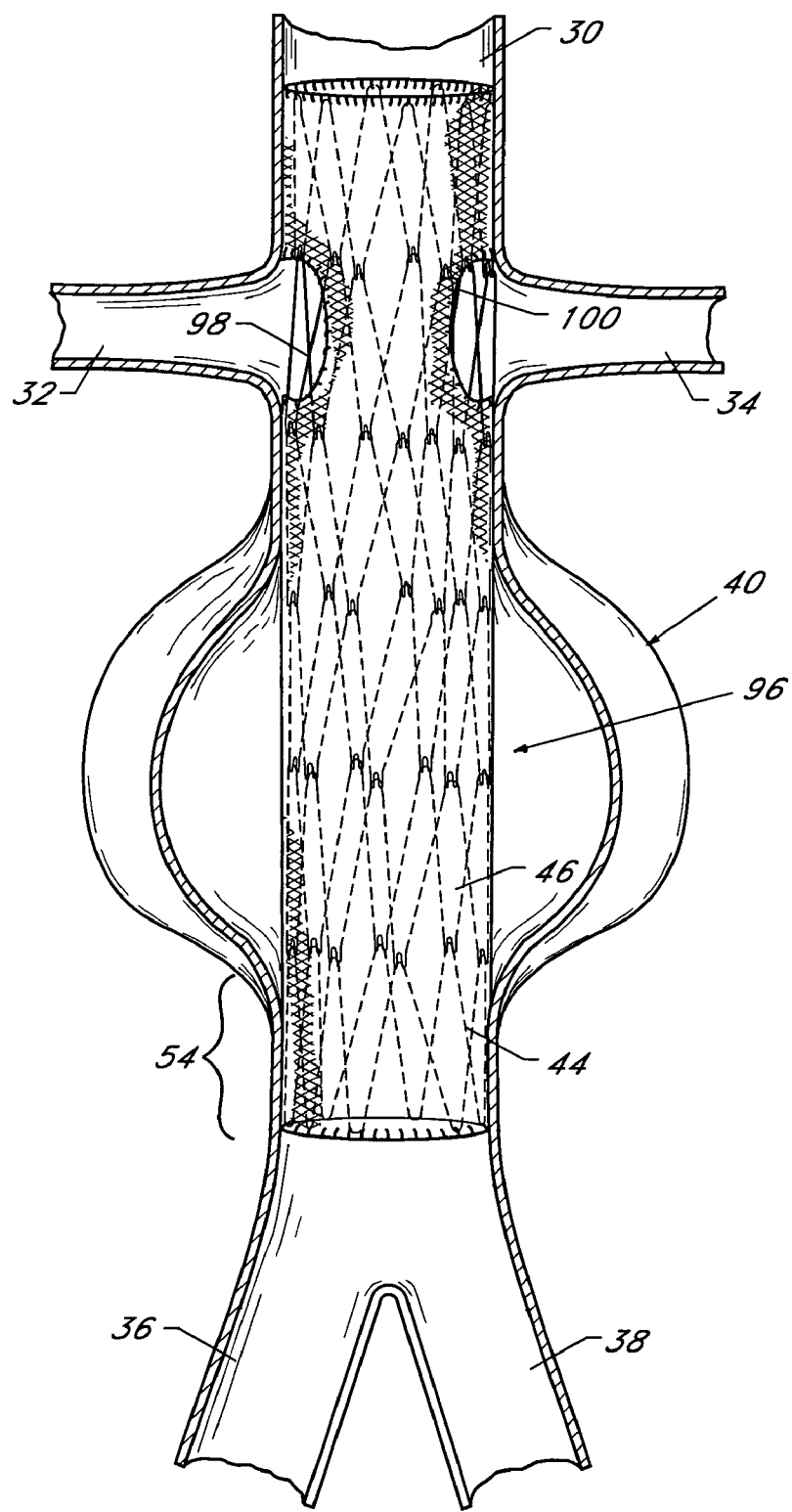
FIG. 19 is a schematic representation of a straight segment graft in accordance with a further embodiment of the present invention, with side openings to permit renal perfusion.

Referring to FIG. 19, there is illustrated a modified embodiment of the endovascular prosthesis 96 in accordance with the present invention. In the embodiment illustrated in FIG. 19, the endovascular prosthesis 96 is provided with a wire cage 46 having six axially aligned segments 54. As with the previous embodiments, however, the endovascular prosthesis 96 may be provided with anywhere from about 2 to about 10 or more axially spaced or adjacent segments 54, depending upon the clinical performance objectives of the particular embodiment.

The wire support 46 is provided with a tubular polymeric sleeve 44 as has been discussed. In the present embodiment, however, one or more lateral perfusion ports or openings are provided in the polymeric sleeve 44, such as a right renal artery perfusion port 98 and a left renal artery perfusion port 100 as illustrated.

Perfusion ports in the polymeric sleeve 44 may be desirable in embodiments of the endovascular prosthesis 96 in a variety of clinical contexts. For example, although FIGS. 1 and 19 illustrate a generally symmetrical aneurysm 40 positioned within a linear infrarenal portion of the abdominal aorta, spaced axially apart both from bilaterally symmetrical right and left renal arteries and bilaterally symmetrical right and left common iliacs, both the position and symmetry of the aneurysm 40 as well as the layout of the abdominal aortic architecture may differ significantly from patient to patient. As a consequence, the endovascular prosthesis 96 may need to extend across one or both of the renal arteries in order to adequately anchor the endovascular prosthesis 96 and/or span the aneurysm 40. The provision of one or more lateral perfusion ports or zones enables the endovascular prosthesis 96 to span the renal arteries while permitting perfusion therethrough, thereby preventing "stent jailing" of the renals. Lateral perfusion through the endovascular prosthesis 96 may also be provided, if desired, for a variety of other arteries including the second lumbar, testicular, inferior mesenteric, middle sacral, and alike as will be well understood to those of skill in the art.

The endovascular prosthesis 96 is preferably provided with at least one, and preferably two or more radiopaque markers, to facilitate proper positioning of the prosthesis 96 within the artery. In an embodiment having perfusion ports 98 and 100 such as in the illustrated design, the prosthesis 96 should be properly aligned both axially and rotationally, thereby requiring the ability to visualize both the axial and rotational position of the device. Alternatively, provided that the delivery catheter design exhibits sufficient torque transmission, the rotational orientation of the graft may be coordinated with an indexed marker on the proximal end of the catheter, so that the catheter may be rotated and determined by an external indicia of rotational orientation to be appropriately aligned with the right and left renal arteries.

In an alternative embodiment, the polymeric sleeve 44 extends across the aneurysm 40, but terminates in the infrarenal zone. In this embodiment, a proximal zone 55 (as illustrated in FIG. 2) on the prosthesis 96 comprises a wire cage 46 but no polymeric sleeve 44. In this embodiment, the prosthesis 96 still accomplishes the anchoring function across the renal arteries, yet does not materially interfere with renal perfusion. Thus, the polymeric sleeve 44 may cover anywhere from about 50% to about 100% of the axial length of the prosthesis 96 depending upon the desired length of uncovered wire cage 46 such as for anchoring and/or lateral perfusion purposes. In particular embodiments, the polymeric sleeve 44 may cover within the range of from about 70% to about 80%, and, in one four segment embodiment having a single exposed segment, 75%, of the overall length of the prosthesis 96. The uncovered wire cage 46 may reside at only a single end of the prosthesis 96, such as for traversing the renal arteries. Alternatively, exposed portions of the wire cage 46 may be provided at both ends of the prosthesis such as for anchoring purposes.

In another embodiment, a two part polymeric sleeve 44 is provided. A first distal part spans the aneurysm 40, and has a proximal end that terminates distally of the renal arteries. A second, proximal part of the polymeric sleeve 44 is carried by the proximal portion of the wire cage 46 that is positioned superiorly of the renal arteries. This leaves an annular lateral flow path through the side wall of the vascular prosthesis 96, which can be axially aligned with the renal arteries, without regard to rotational orientation.

The axial length of the gap between the proximal and distal segments of polymeric sleeve 44 can be adjusted, depending upon the anticipated cross-sectional size of the ostium of the renal artery, as well as the potential axial misalignment between the right and left renal arteries. Although the right renal artery 32 and left renal artery 34 are illustrated in FIG. 19 as being concentrically disposed on opposite sides of the abdominal aorta, the take off point for the right or left renal arteries from the abdominal aorta may be spaced apart along the abdominal aorta as will be familiar to those of skill in the art. In general, the diameter of the ostium of the renal artery measured in the axial direction along the abdominal aorta falls within the range of from about 7 mm to about 20 mm for a typical adult patient.

Prior art procedures presently use a 7 mm introducer (18 French) which involves a surgical procedure for introduction of the graft delivery device. Embodiments of the present invention can be constructed having a 16 French or 15 French or 14 French or smaller profile (e.g., 3-4 mm) thereby enabling placement of the endolumenal vascular prosthesis of the present invention by way of a percutaneous procedure. In addition, the endolumenal vascular prosthesis of the present invention does not require a post implantation balloon dilatation, can be constructed to have minimal axial shrinkage upon radial expansion.

Figure 20:
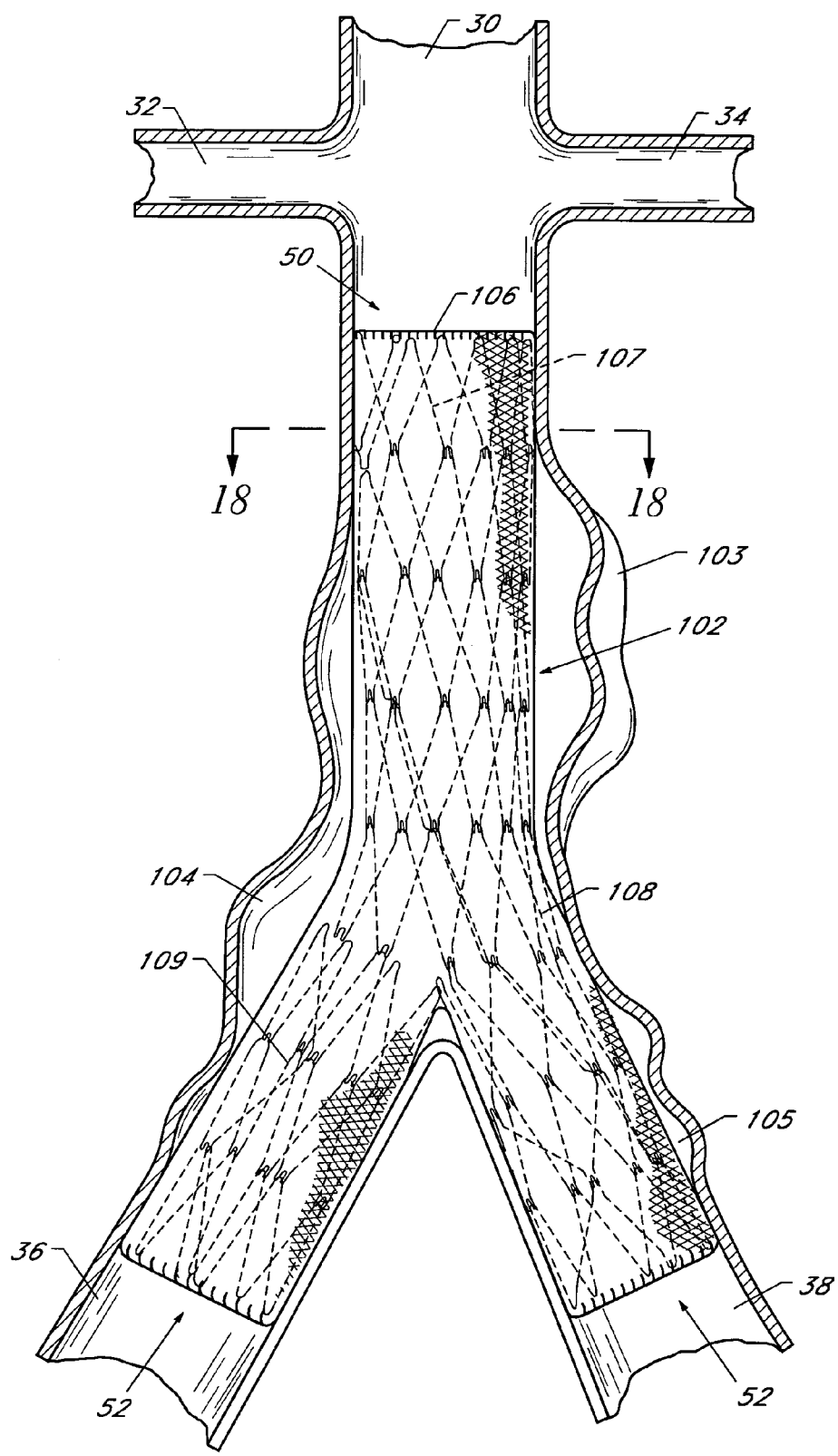
FIG. 20 is a schematic representation of a bifurcated vascular prosthesis in accordance with the present invention, positioned at the bifurcation between the abdominal aorta and the right and left common iliac arteries.

Referring to FIG. 20, there is disclosed a schematic representation of the abdominal part of the aorta and its principal branches as in FIG. 1. An expanded bifurcated endolumenal vascular prosthesis 102, in accordance with one embodiment, is illustrated spanning the aneurysms 103, 104 and 105. In addition, to the description below, reference is made to U.S. Pat. Nos. 6,660,030, 6,187,036 and 6,197,049, which are hereby incorporated by reference herein in their entirety. The illustrated endolumenal vascular prosthesis 102 includes a polymeric sleeve 106 and a tubular wire support 107, which are illustrated in situ in FIG. 20. The sleeve 106 and wire support 107 are more readily visualized in the exploded view shown in FIG. 21 and the cross-sectional view of FIG. 22. The endolumenal prosthesis 102 illustrated and described herein depicts an embodiment in which the polymeric sleeve 106 is situated concentrically outside of the tubular wire support 107. However, other embodiments may include a sleeve situated instead concentrically inside the wire support or on both of the inside and the outside of the wire support. Alternatively, the wire support may be embedded within a polymeric matrix that makes up the sleeve. Regardless of whether the sleeve 106 is inside or outside the wire support 107, the sleeve may be attached to the wire support by any of a variety of methods or devices, as has been previously discussed.

The tubular wire support 107 comprises a primary component 108 for traversing the aorta and a first iliac, and a branch component 109 for extending into the second iliac. The primary component 108 may be formed from a continuous single length of wire, throughout both the aorta trunk portion and the iliac branch portion. See FIGS. 20 and 23. Alternatively, each iliac branch component can be formed separately from the aorta trunk portion. Construction of the graft from a three part cage conveniently facilitates the use of different gauge wire in the different components (e.g., 14 gauge main trunk and 10 gauge branch components).

Figure 23:
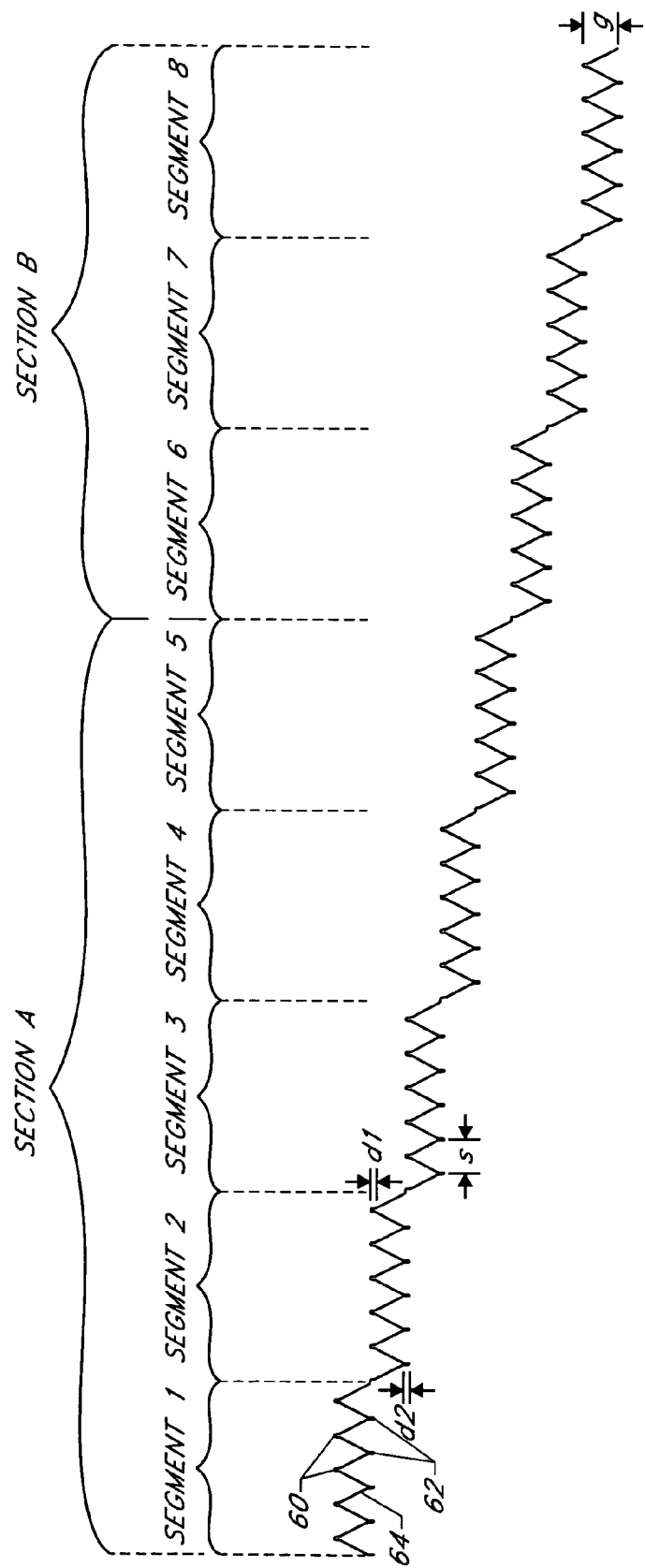
FIG. 23 is a plan view of formed wire useful for rolling about an axis into an aortic trunk segment and a first iliac branch segment support structure in accordance with the present invention.

The wire support 107 is preferably formed in a plurality of discrete segments, connected together and oriented about a common axis. In FIG. 23, Section A corresponds to the aorta trunk portion of the primary component 108, and includes segments 1-5. Segments 6-8 (Section B) correspond to the iliac branch portion of the primary component 108.

In general, each of the components of the tubular wire support 107 can be varied considerably in diameter, length, and expansion coefficient, depending upon the intended application. For implantation within a typical adult, the aorta trunk portion (section A) of primary component 108 will have a length within the range of from about 5 cm to about 12 cm, and, typically within the range of from about 9 cm to about 10 cm. The unconstrained outside expanded diameter of the section A portion of the primary component 108 will typically be within the range of from about 20 mm to about 40 mm. The unconstrained expanded outside diameter of the section A portion of primary component 108 can be constant or substantially constant throughout the length of section A, or can be tapered from a relatively larger diameter at the proximal end to a relatively smaller diameter at the bifurcation. In general, the diameter of the distal end of section A will be on the order of no more than about 95% and, preferably, no more than about 85% of the diameter of the proximal end of section A.

The right and left iliac portions, corresponding to section B on primary component 108 and section C will typically be bilaterally symmetrical. Section C length will generally be within the range of from about 1 cm to about 5 cm, and section C diameter will typically be within the range of from about 10 mm to about 20 mm.

Referring to FIG. 21, the wire cage 107 is dividable into a proximal zone 110, a central zone 111 and a distal zone 112. As has been discussed, the wire cage 107 can be configured to taper from a relatively larger diameter in the proximal zone 110 to a relatively smaller diameter in the distal zone 112. In addition, the wire cage 107 can have a transitional tapered and or stepped diameter within a given zone.

Referring to FIG. 23, there is illustrated a plan view of the single formed wire used for rolling about a longitudinal axis to produce a primary segment 108 having a five segment aorta section and a three segment iliac section. The formed wire exhibits distinct segments, each corresponding to an individual tubular segment in the tubular support. Additional details of the wire cage layout and construction can be found in co-pending U.S. patent application Ser. No. 09/034,689 entitled Endolumenal Vascular Prosthesis, filed Mar. 4, 1998, the disclosure of which is incorporated in its entirety herein by reference.

Each segment has a repeating pattern of proximal bends 60 connected to corresponding distal bends 62 by wall sections 64 which extend in a generally zig-zag configuration when the segment is radially expanded, as has been discussed in connection with FIG. 3. Each segment is connected to the adjacent segment through a connector 66, and one or more links 70 as has been discussed in connection with FIGS. 5-12. The connector 66 in the illustrated embodiment comprises two wall sections 64 which connect a proximal bend 60 on a first segment with a distal bend 62 on a second, adjacent segment. The connector 66 may additionally be provided with a connector bend 68, which may be used to impart increased radial strength to the graft and/or provide a tie site for a circumferentially extending suture.

In the illustrated embodiment, section A is intended for deployment within the aorta whereas section B is intended to be deployed within a first iliac. Thus, section B will preferably have a smaller expanded diameter than section A. This may be accomplished by providing fewer proximal and distal bends 60, 62 per segment in section B or in other manners as will be apparent to those of skill in the art in view of the disclosure herein. In the illustrated embodiment, section B has one fewer proximal bend 60 per segment than does each segment in section A. This facilitates wrapping of the wire into a tubular prosthesis cage such as that illustrated in FIG. 22, so that the iliac branch has a smaller diameter than the aorta branch. At the bifurcation, an opening remains for connection of the second iliac branch. The second branch is preferably formed from a section of wire in accordance with the general principles discussed above, and in a manner that produces a similarly dimensioned wire cage as that produced by section B. The second iliac branch (section C) may be attached at the bifurcation to section A and/or section B in any of a variety of manners, to provide a secure junction therebetween. In one embodiment, one or two of the proximal bends 60 on section C will be secured to the corresponding distal bends 62 on the distal most segment of section A. Attachment may be accomplished such as through the use of a circumferentially threaded suture, through links 70 as has been discussed previously, through soldering or other attachment method or device. The attachment method or device will be influenced by the desirable flexibility of the graft at the bifurcation, which will in turn be influenced by the method of deployment of the vascular graft as will be apparent to those of skill in the art in view of the disclosure herein.

Figure 24:
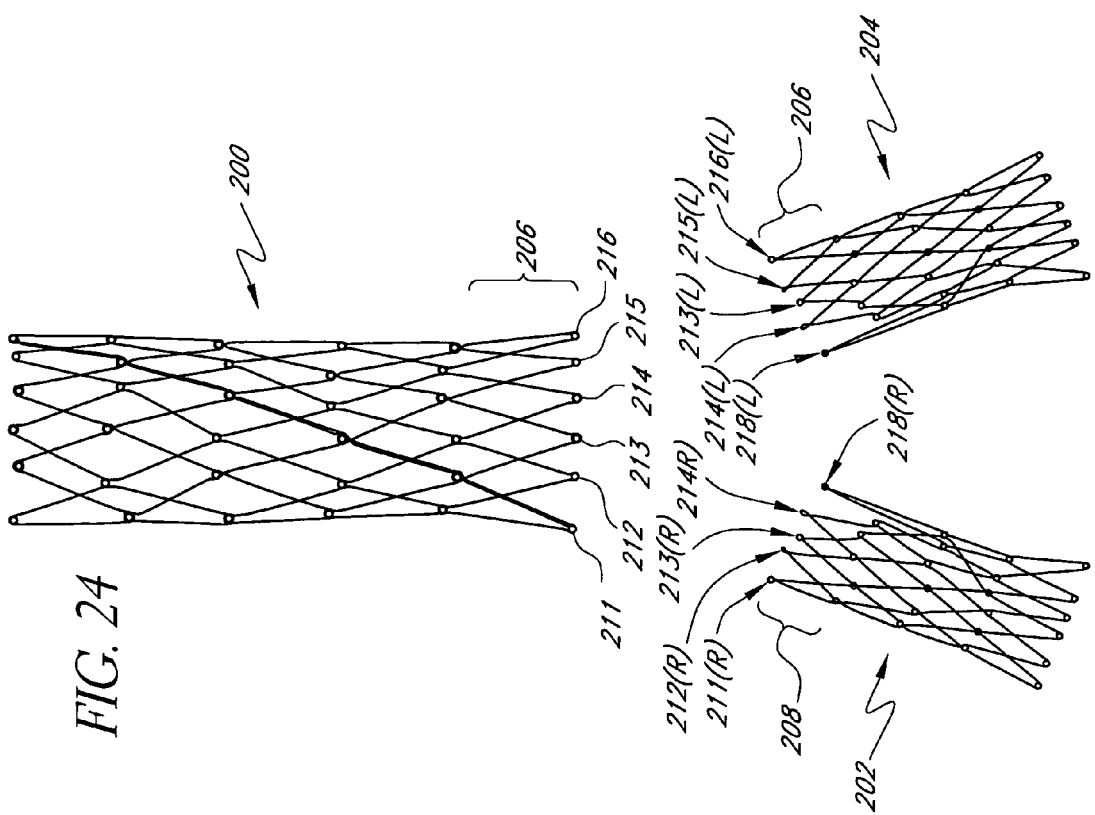
FIG. 24 is a schematic representation of another embodiment of the wire support structure for the bifurcated vascular prosthesis of the present invention, showing a main body support structure and separate branch support structures.

Referring to FIG. 24, there is disclosed an exploded schematic representation of a hinged or articulated variation in the tubular wire support structure for a bifurcated graft in accordance with present invention. The tubular wire support comprises a main body, or aortic trunk portion 200 and right 202 and left 204 iliac branch portions. Right and left designations correspond to the anatomic designations of right and left common iliac arteries. The proximal end 206 of the aortic trunk portion 200 has apexes 211-216 adapted for connection with the complementary apexes on the distal ends 208 and 210 of the right 202 and left 204 iliac branch portions, respectively. Complementary pairing of apexes is indicated by the shared numbers, wherein the right branch portion apexes are designated by (R) and the left branch portion apexes are designated by (L). Each of the portions may be formed from a continuous single length of wire. See FIG. 26.

Figure 25:
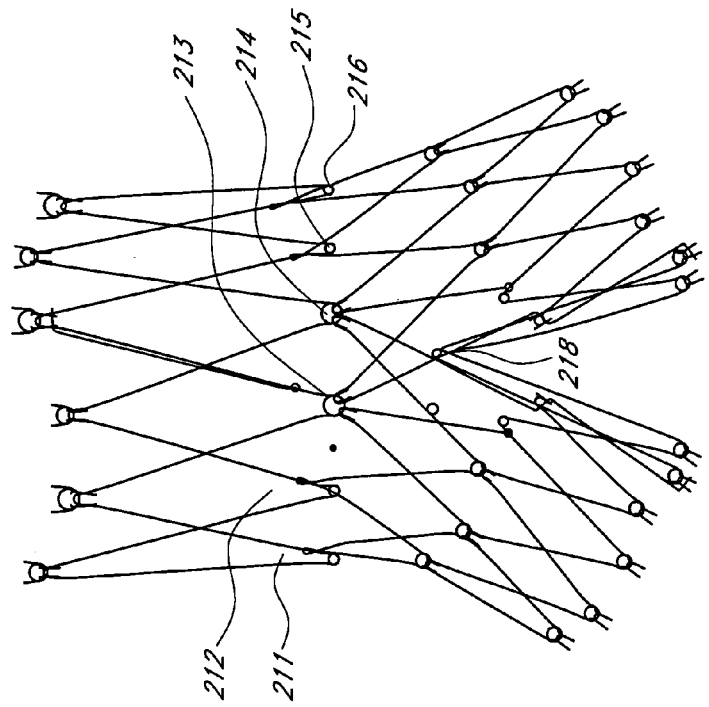
FIG. 25 is a schematic representation of the three-part wire support structure as in FIG. 24, illustrating the sliding articulation between the branch supports and the main body support.

Referring to FIG. 25, the assembled articulated wire support structure is shown. The central or medial apex 213 in the foreground (anterior) of the aortic trunk portion 200 is linked with 213(R) on the right iliac portion 202 and 213(L) on the left iliac portion 204. Similarly, the central apex 214 in the background (posterior) is linked with 214(R) on the right iliac portion 202 and 214(L) on the left iliac portion 204. Each of these linkages has two iliac apexes joined with one aortic branch apex. The linkage configurations may be of any of the variety described above in FIG. 7A-D. The medial most apexes 218 (R) and (L) of the iliac branch portions 202 and 204 are linked together, without direct connection with the aortic truck portion 200.

The medial apexes 213 and 214 function as pivot points about which the right and left iliac branches 202, 204 can pivot to accommodate unique anatomies. Although the right and left iliac branches 202, 204 are illustrated at an angle of about 45° to each other, they are articulable through at least an angle of about 90° and preferably at least about 120°. The illustrated embodiment allows articulation through about 180° while maintaining patency of the central lumen. To further improve patency at high iliac angles, the apexes 213 and 214 can be displaced proximally from the transverse plane which roughly contains apexes 211, 212, 215 and 216 by a minor adjustment to the fixture about which the wire is formed. Advancing the pivot point proximally relative to the lateral apexes (e.g., apexes 211, 216) opens the unbiased angle between the iliac branches 202 and 204.

In the illustrated embodiment, the pivot point is formed by a moveable link between an eye on apex 213 and two apexes 213R and 213L folded therethrough. To accommodate the two iliac apexes 213R and 213L, the diameter of the eye at apex 213 may be slightly larger than the diameter of the eye on other apexes throughout the graft. Thus, for example, the diameter of the eye at apex 213 in one embodiment made from 0.014" diameter wire is about 0.059", compared to a diameter of about 0.020" for eyes elsewhere in the graft.

Although the pivot points (apexes 213, 214) in the illustrated embodiment are on the medial plane, they may be moved laterally such as, for example, to the axis of each of the iliac branches. In this variation, each iliac branch will have an anterior and a posterior pivot link on or about its longitudinal axis, for a total of four unique pivot links at the bifurcation. Alternatively, the pivot points can be moved as far as to lateral apexes 211 and 216. Other variations will be apparent to those of skill in the art in view of the disclosure herein.

To facilitate lateral rotation of the iliac branches 202, 204 about the pivot points and away from the longitudinal axis of the aorta trunk portion 200 of the graft, the remaining links between the aorta trunk portion 200 and the iliac branches 202, 204 preferably permit axial compression and expansion.

In general, at least one and preferably several links lateral to the pivot point in the illustrated embodiment permit axial compression or shortening of the graft to accommodate lateral pivoting of the iliac branch. If the pivot point is moved laterally from the longitudinal axis of the aorta portion of the graft, any links medial of the pivot point preferably permit axial elongation to accommodate lateral rotation of the branch. In this manner, the desired range of rotation of the iliac branches may be accomplished with minimal deformation of the wire, and with patency of the graft optimized throughout the angular range of motion.

To permit axial compression substantially without deformation of the wire, the lateral linkages, 211 and 212 for the right iliac, and 215 and 216 for the left iliac, may be different from the previously described apex-to-apex linkage configurations. The lateral linkages are preferably slidable linkages, wherein a loop formed at the distal end of the iliac apex slidably engages a strut of the corresponding aortic truck portion. The loop and strut orientation may be reversed, as will be apparent to those of skill in the art. Interlocking "elbows" without any distinct loop may also be used. Such an axially compressible linkage on the lateral margins of the assembled wire support structure allow the iliac branch portions much greater lateral flexibility, thereby facilitating placement in patients who often exhibit a variety of iliac branch asymmetries and different angles of divergence from the aortic trunk.

Referring to FIG. 26, there is illustrated a plan view of a single formed wire used for rolling about a longitudinal axis to produce a four segment straight tubular wire support for an iliac limb. The formed wire exhibits distinct segments, each corresponding to an individual tubular segment in the tubular supports 202 or 204 (See FIG. 24). The distal segment I, is adapted to articulate with the aortic trunk portion 200 and the adjacent iliac limb portion. The distal segment (I) has two apexes (e.g., corresponding to 211 and 212 on the right iliac portion 202 in FIG. 23) which form a loop adapted to slidably engage a strut in the lateral wall of the aortic portion. These articulating loops (A) are enlarged in FIG. 27A. As discussed above, the loops are preferably looped around a strut on the corresponding apex of the proximal aortic segment to provide a sliding linkage.

The apex 218 is proximally displaced relative to the other four apexes in the distal segment (I). Apex 218 (R or L) is designed to link with the complementary 218 apex on the other iliac branch portion (See FIG. 25). The apex 218 in the illustrated embodiment is formed adjacent or near an inter-segment connector 66, which extends proximally from the distal segment.

The other apexes on the distal segment (I) of an iliac limb are designed to link with a loop on the corresponding apex of the proximal aortic segment. Because many variations of this linkage are consistent with the present invention (See FIGS. 7A-D), the form of the corresponding apexes may vary. In a preferred variation, the apexes (B) form a narrow U-shape, having an inside diameter of about 0.019 inches in an embodiment made from 0.012 inch Conichrome wire (tensile strength 300 ksi minimum) as illustrated in FIG. 27B. The U-shaped, elongated axial portion of the apex shown in FIG. 25B permits the apex to be wrapped through and around a corresponding loop apex of the proximal aortic segment. This type of linkage is discussed in greater detail above in connection with FIGS. 5 and 6.

In more general terms, the wire support illustrated in FIGS. 24 and 25 comprises a main body support structure formed from one or more lengths of wire and having a proximal end, a distal end and a central lumen extending along a longitudinal axis. The wire support also comprises a first branch support structure formed from one or more lengths of wire and having a proximal end, a distal end and a central lumen therethrough. The first branch support structure is pivotably connected to the proximal end of the main body support structure. The tubular wire support further comprises a second branch support structure formed from one or more lengths of wire and having a proximal end, a distal end and a central lumen extending therethrough. The distal end of the second branch support structure is pivotably connected to the proximal end of the main body support structure.

Further, the distal ends of the first and second branch structures may be joined together by a flexible linkage, formed for example between apexes 218(R) and 218(L) in FIG. 24. By incorporating a medial linkage between the two branch support structures and pivotable linkages with the main trunk, the first and second branch support structures can hinge laterally outward from the longitudinal axis without compromising the volume of the lumen. Thus, the branches may enjoy a wide range of lateral movement, thereby accommodating a variety of patient and vessel heterogeneity. Additional corresponding apexes between the main trunk and each iliac branch may also be connected, or may be free floating within the outer polymeric sleeve. Axially compressible lateral linkages, discussed above and illustrated in FIG. 25, may optionally be added.

The proximal apexes (C) of the iliac limb portions are adapted to link with the distal apexes of the next segment. These proximal apexes preferably form loops, such as those illustrated in FIG. 27C, wherein the elongated axial portions of the corresponding proximal apex in the adjacent segment can wrap around the loop, thereby providing flexibility of the graft, as discussed above for FIGS. 5 and 6.

The wire may be made from any of a variety of different alloys and wire diameters or non-round cross-sections, as has been discussed. In one embodiment of the bifurcation graft, the wire gauge remains substantially constant throughout section A of the primary component 49 and steps down to a second, smaller cross-section throughout section B of primary component 108.

A wire diameter of approximately 0.018 inches may be useful in the aorta trunk portion of a graft having five segments each having 2.0 cm length per segment, each segment having six struts intended for use in the aorta, while a smaller diameter such as 0.012 inches might be useful for segments of the graft having 6 struts per segment intended for the iliac artery.

In one embodiment of the present invention, the wire diameter may be tapered throughout from the proximal to distal ends of the section A and/or section B portions of the primary component 108. Alternatively, the wire diameter may be tapered incremental or stepped down, or stepped up, depending on the radial strength requirements of each particular clinical application. In one embodiment, intended for the abdominal aortic artery, the wire has a cross-section of about 0.018 inches in the proximal zone 110 and the wire tapers down regularly or in one or more steps to a diameter of about 0.012 inches in the distal zone 112 of the graft 102. End point dimensions and rates of taper can be varied widely, within the spirit of the present invention, depending upon the desired clinical performance.

In general, in the tapered or stepped wire embodiments, the diameter of the wire in the iliac branches is no more than about 80% of the diameter of the wire in the aortic trunk. This permits increased flexibility of the graft in the region of the iliac branches, which has been determined by the present inventors to be clinically desirable.

The collapsed prosthesis in accordance with the present invention has a diameter in the range of about 2 to about 10 mm. Preferably, the maximum diameter of the collapsed prosthesis is in the range of about 3 to 6 mm (12 to 18 French). Some embodiments of the delivery catheter including the prosthesis will be in the range of from 18 to 20 or 21 French; other embodiments will be as low as 19 F, 16 F, 14 F, or smaller. After deployment, the expanded endolumenal vascular prosthesis has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

As described above in detail with respect to the linkage of stent segments using the polymeric sleeve, the same construction and methods are applicable to the flexible bifurcated wire cage just described. Thus, the bifurcated stent can be coated on the lumenal side, the external side, or preferably embedded within layers of porous, expandable polymeric material, as described above.

The self-expandable bifurcation graft of the present invention can be deployed at a treatment site in accordance with any of a variety of techniques as will be apparent to those of skill in the art. One such technique is disclosed in co-pending patent application Ser. No. 08/802,478 entitled Bifurcated Vascular Graft and Method and Apparatus for Deploying Same, filed Feb. 20, 1997, the disclosure of which is incorporated in its entirety herein by reference.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the he scope of the claims.

What is claimed is:

1. An endolumenal prosthesis having a lumenal surface and an ablumenal surface, comprising:
    a tubular wire support with proximal and distal ends and a central lumen extending therebetween, the wire support comprising at least two axially adjacent tubular segments, each segment comprising a series of proximal and distal bends connected by a length of wire, wherein the wire support is radially compressible into a first, reduced cross sectional configuration for translumenal navigation to a treatment site in a body lumen and self expandable to a second, enlarged cross sectional configuration for deployment at the treatment site in the body lumen; and
    a uniform porous tubular ePTFE sheath on the wire support, the tubular sheath having a sheath proximal end region and a sheath distal end region, wherein the sheath is porous and configured to inhibit sufficient cellular ingrowth through the wall of the sheath that would permit the formation of a viable neointimal layer on the lumenal surface of the sheath at the sheath proximal and distal end regions without a coating on the sheath that would inhibit cellular ingrowth,
    wherein the sheath is formed from a single ply of ePTFE and wherein a wall thickness of the sheath is the thickness of the single ply of ePTFE.

2. The endolumenal prosthesis of claim 1, wherein the ePTFE sheath wall thickness is no greater than about 0.2 mm.

3. The endolumenal prosthesis of claim 2, wherein the ePTFE sheath wall thickness is about 0.1 mm.

4. The endolumenal prosthesis of claim 2, comprising at least three segments.

5. The endolumenal prosthesis of claim 2, comprising at least five segments.

6. The endolumenal prosthesis of claim 2, wherein each segment comprises from about 4 proximal bends to about 12 proximal bends.

7. The endolumenal prosthesis of claim 2, wherein at least the first and second axially adjacent tubular segments are joined by at least one folded link extending therebetween.

8. The endolumenal prosthesis of claim 7, wherein the first tubular segment includes two side-by-side legs with a first apex thereon and the folded link is formed by folding around the first apex around a second apex formed on the second tubular segment.

9. The endolumenal prosthesis of claim 1, wherein the ePTFE sheath wall thickness is within the range of from about 0.05 mm to about 0.15 mm.

10. The endolumenal prosthesis of claim 9, wherein the ePTFE sheath has a density within the range of from about 1.1 to about 1.5 grams per milliliter.

11. The endolumenal prosthesis of claim 9, wherein the ePTFE sheath has a plurality of nodes, and the average distance between nodes is within the range of from about 6 microns to about 80 microns.

12. The endolumenal prosthesis of claim 9, wherein the ePTFE sheath has a density of at least about 0.75 grams per milliliter.

13. The endolumenal prosthesis of claim 12, wherein the ePTFE sheath has a plurality of nodes, and the average distance between nodes is within the range of from about 6 microns to about 80 microns.

14. The endolumenal prosthesis of claim 1, wherein the ePTFE sheath has a density of at least about 0.5 grams per milliliter.

15. The endolumenal prosthesis of claim 1, wherein the ePTFE sheath has a plurality of nodes, and the average distance between nodes is within the range of from about 6 microns to about 80 microns.

16. The endolumenal prosthesis of claim 1, wherein the ePTFE sheath has a water entry pressure in the range of from about 10 psi to about 24 psi.

17. A bifurcated endolumenal prosthesis having a lumenal surface and an ablumenal surface, comprising:
    a proximal wire support section having a proximal end, a distal end and a central lumen extending therethrough, the proximal support section comprising at least two axially adjacent tubular segments comprising a series of distal and proximal bends connected by struts;
    a first wire branch section at the distal end of the proximal support;
    a second wire branch section at the distal end of the proximal support; and
    a uniform porous membrane carried by the wire support section, the membrane having a membrane proximal end region and membrane distal end regions and configured to inhibit cellular growth through the membrane that would be sufficient to enable the formation of a thin, viable neointimal layer on the lumenal surface of the membrane at least at the membrane proximal and distal end regions without a coating on the membrane that would inhibit cellular ingrowth, the membrane consists of and has a thickness of a single ply of ePTFE.

18. A prosthetic vascular graft, comprising:
    an expandable tubular wire support;
    a uniform porous, tubular ePTFE layer carried by the support, the ePTFE layer formed from a single ply of ePTFE and having:

a wall thickness equal to a thickness of the single ply of ePTFE and less than about 0.15 millimeters;

an average density of greater than about 0.75 grams per milliliter; and an average distance between nodes in the range of between about 6 to about 80 microns;

so that the uniform porous ePTFE layer prevents the formation and nourishment of a viable neointimal layer therethrough along portions of the tubular ePTFE layer's axial length, which are in contact with a vessel wall.

19. An artificial vascular prosthesis comprising an enlargeable support structure having an expanded, uniform porous, polytetrafluoroethylene layer thereon, the layer consisting of a single ply of polytetrafluoroethylene and having a wall thickness equal to the thickness of the single ply of polytetrafluoroethylene and a microstructure consisting of nodes interconnected by fibrils which prevents tissue ingrowth through portions of the layer that contact a vessel wall when the prosthesis is implanted to span an aneurysm, in which either the density is greater than about 1 gram per milliliter or the wall thickness is less than about 0.2 millimeters, or both.

20. A method of treating a patient, comprising:
providing an implantable tubular prosthesis, having a uniform porous ePTFE layer formed from a single ply of ePTFE thereon, the porous ePTFE layer having a wall thickness equal to the thickness of the single ply of ePTFE, a proximal end and a distal end;

positioning the prosthesis across a defect in a vessel such that a contacting portion of a first side of the layer is in contact with the wall of the vessel; thereby inhibiting formation of a viable neointima on a second side of the layer throughout the contacting portion, nourished through the layer;

wherein said inhibiting step is a result of the ePTFE layer having a density of greater than about 0.75 grams per milliliter and a wall thickness of less than 0.2 mm.

21. An endolumenal prosthesis having a lumenal surface and an ablumenal surface, comprising:
a tubular wire support with proximal and distal ends and a central lumen extending therebetween, the wire support comprising at least two axially adjacent tubular segments, each segment comprising a series of proximal and distal bends wherein the wire support is radially compressible into a first, reduced cross sectional configuration for translumenal navigation to a treatment site in a body lumen and self expandable to a second, enlarged cross sectional configuration for deployment at the treatment site in the body lumen; and a uniform porous, tubular ePTFE sheath on the wire support, the porous, tubular sheath being formed from a single ply of ePTFE and having a wall thickness equal to the thickness of the single ply of ePTFE, the tubular sheath having a proximal end and a distal end and being configured to have a water entry pressure of at least about 10 psi, and wherein the uniform porous tubular sheath is configured to inhibit the formation of a viable neointimal layer on the lumenal surface of the without a coating on the sheath that would inhibit cellular ingrowth.

22. The endolumenal prosthesis of claim 21, wherein the ePTFE sheath wall thickness is no greater than about 0.2 mm.

23. The endolumenal prosthesis of claim 22, wherein the ePTFE sheath wall thickness is about 0.1 mm.

24. The endolumenal prosthesis of claim 21, wherein the ePTFE sheath wall thickness is within the range of from about 0.05 mm to about 0.15 mm.

25. The endolumenal prosthesis of claim 24, wherein the ePTFE sheath has a density within the range of from about 1.1 to about 1.5 grams per milliliter.

26. The endolumenal prosthesis of claim 24, wherein the ePTFE sheath has a plurality of nodes, and the average distance between nodes is within the range of from about 6 microns to about 80 microns.

27. The endolumenal prosthesis of claim 24, wherein the ePTFE sheath has a density of at least about 0.75 grams per milliliter.

28. The endolumenal prosthesis of claim 27, wherein the ePTFE sheath has a plurality of nodes, and the average distance between nodes is within the range of from about 6 microns to about 80 microns.

29. The endolumenal prosthesis of claim 21, wherein the ePTFE sheath has a density of at least about 0.5 grams per milliliter.

30. The endolumenal prosthesis of claim 21, wherein the ePTFE sheath has a plurality of nodes, and the average distance between nodes is within the range of from about 6 microns to about 80 microns.

31. The endolumenal prosthesis of claim 21, wherein the tubular sheath is further configured to inhibit the formation of a viable neointimal layer on the lumenal surface of the sheath at the distal end.

32. The endolumenal prosthesis of claim 21, wherein the proximal end comprises a single opening and the distal end comprises two openings, such that the prosthesis is configured for implantation at a vascular bifurcation.

* * * * *

UNITED STATES PATENT AND TRADEMARK OFFICE
CERTIFICATE OF CORRECTION

| | | |
|---|---|---|
| PATENT NO. | : 8,377,110 B2 | Page 1 of 1 |
| APPLICATION NO. | : 10/820455 | |
| DATED | : February 19, 2013 | |
| INVENTOR(S) | : Douglas et al. | |

It is certified that error appears in the above-identified patent and that said Letters Patent is hereby corrected as shown below:

In the Specifications:

In column 6 at line 6, after "substantially" insert --concentrically inside the wire support 46, or on both the inside and the outside of the wire--.

In column 9 at line 40, change "44." to --44--.

In column 16 at line 38, change "0.82Δ." to --0.82".--.

In column 29 at line 35, change "he" to --spirit of the invention or the--.

In the Claims:

In column 30 at line 61, in Claim 17, after "ingrowth," insert --wherein--.

In column 32 at line 9, in Claim 21, after "of the" insert --sheath through the wall of the sheath--.

Signed and Sealed this
Thirteenth Day of August, 2013

Teresa Stanek Rea
*Acting Director of the United States Patent and Trademark Office*